United States Patent
Seemakurty et al.

(10) Patent No.: US 11,195,616 B1
(45) Date of Patent: Dec. 7, 2021

(54) SYSTEMS AND METHODS USING ENSEMBLE MACHINE LEARNING TECHNIQUES FOR FUTURE EVENT DETECTION

(71) Applicant: Stasis Labs, Inc., Marina del Rey, CA (US)

(72) Inventors: Dinesh Seemakurty, Irving, TX (US); Michael Andrew Maylahn, Los Angeles, CA (US); Mark William Davis, Port Orange, FL (US); Roheet Bantval Rao, Bangalore (IN); Aditya Patel, Madhya Pradesh (IN); Izzatbir Singh, Punjab (IN); Aashay Sachdeva, Uttar Pradesh (IN)

(73) Assignee: Stasis Labs, Inc., Marina del Rey, CA (US)

( * ) Notice: Subject to any disclaimer, the term of this patent is extended or adjusted under 35 U.S.C. 154(b) by 0 days.

(21) Appl. No.: 17/071,957

(22) Filed: Oct. 15, 2020

(51) Int. Cl.
*G16H 40/67* (2018.01)
*G16H 10/60* (2018.01)
(Continued)

(52) U.S. Cl.
CPC .......... *G16H 40/67* (2018.01); *A61B 5/0022* (2013.01); *A61B 5/02055* (2013.01);
(Continued)

(58) Field of Classification Search
CPC ........ G16H 40/60; G16H 40/67; G16H 10/60; G16H 50/30; G16H 50/20; G06N 20/20;
(Continued)

(56) References Cited

U.S. PATENT DOCUMENTS 10,433,726 B2 10/2019 Ramesh et al.
2008/0214904 A1\* 9/2008 Saeed .................. G16H 50/30
600/301

(Continued)

FOREIGN PATENT DOCUMENTS

IN 204023 B 5/2007
IN 243523 B 10/2010
(Continued)

OTHER PUBLICATIONS

Nora El-Rashidy, et al., Intensive Care Unit Mortality Prediction: An Improved Patient-Specific Stacking Ensemble Model, Jul. 30, 2020, IEEE Access, vol. B, 2020, pp. 133541-133564 (Year: 2020).\*

(Continued)

*Primary Examiner* — Evangeline Barr
(74) *Attorney, Agent, or Firm* — Wilson Sonsini Goodrich & Rosati

(57) ABSTRACT

Disclosed herein are platforms, systems, devices, software, and methods for processing and analyzing real-time data to generate predictions of near future events. Machine learning algorithms can be configured for varying levels of aggression to enhance timeliness of the predictions. Ensemble machine learning techniques combining a plurality of trained models configured with higher and lower aggression levels can be used to improve both timeliness and accuracy.

18 Claims, 10 Drawing Sheets

(51) Int. Cl.
*G16H 50/70* (2018.01)
*G16H 70/60* (2018.01)
*G16H 50/20* (2018.01)
*G16H 50/30* (2018.01)
*G06N 20/20* (2019.01)
*G06N 5/00* (2006.01)
*G16H 70/20* (2018.01)
*G16H 40/20* (2018.01)
*A61B 5/145* (2006.01)
*A61B 5/0205* (2006.01)
*A61B 5/00* (2006.01)
*A61B 5/318* (2021.01)
*A61B 5/024* (2006.01)
*A61B 5/08* (2006.01)
*A61B 5/021* (2006.01)

(52) U.S. Cl.
CPC .......... *A61B 5/14542* (2013.01); *A61B 5/318* (2021.01); *A61B 5/7267* (2013.01); *A61B 5/7275* (2013.01); *A61B 5/742* (2013.01); *A61B 5/746* (2013.01); *G06N 5/003* (2013.01); *G06N 20/20* (2019.01); *G16H 10/60* (2018.01); *G16H 40/20* (2018.01); *G16H 50/20* (2018.01); *G16H 50/30* (2018.01); *G16H 50/70* (2018.01); *G16H 70/20* (2018.01); *G16H 70/60* (2018.01); *A61B 5/021* (2013.01); *A61B 5/024* (2013.01); *A61B 5/0816* (2013.01)

(58) Field of Classification Search
CPC .... G06N 5/003; A61B 5/7267; A61B 5/7275; A61B 5/742; A61B 5/746
See application file for complete search history.

(56) References Cited

U.S. PATENT DOCUMENTS

2014/0243612 A1    8/2014  Li et al.
2015/0106020 A1*   4/2015  Chung ................... G16H 40/67
                                                        702/19
2015/0302538 A1   10/2015  Mazar et al.
2017/0301109 A1   10/2017  Chan et al.
2019/0320988 A1   10/2019  Ahmed et al.
2019/0341135 A1   11/2019  Whiting et al.
2020/0178907 A1*   6/2020  Belle .................... A61B 5/0472
2020/0337648 A1*  10/2020  Saripalli ............... A61B 5/7275

FOREIGN PATENT DOCUMENTS

IN              27553 B      9/2016
IN             278006 B      9/2016
IN             324904 B     11/2019
WO     WO-02078783 A2       10/2002
WO     WO-2004027676 A2      4/2004
WO     WO-2007012998 A1      2/2007
WO     WO-2007017777 A2      2/2007
WO     WO-2016044125 A2      3/2016
WO     WO-2019159189 A1      8/2019
WO     WO-2019186194 A2 *   10/2019   ............ G16C 20/70

OTHER PUBLICATIONS

Yawen Xiao, et al.; "A deep learning-based multi-model ensemble method for cancer prediction"; Sep. 6, 2017; Computer Methods and Programs in Biomedicine, 153 (2018) 1-9 (Year: 2017).*
Brand et al.: Real Time Mortality Risk Prediction: A Convolutional Neural Network Approach. Biomedical Engineering Systems and Technologies. vol. 5:463-470 (2018).
Indian Application No. IN201611028804; filed Aug. 24, 2016.
Indian Application No. IN201727007240; filed Mar. 1, 2017.
Indian Application No. IN201921006217; filed Feb. 17, 2019.
Patel et al.: A Weighted Similarity Measure Approach to Predict Intensive Care Unit Transfers. IEEE International Conference on Bioinformatics and Biomedicine (BIBM). 1:1079-1084 DOI:10.1109/BIBM.2017.8217806 (2017).

* cited by examiner

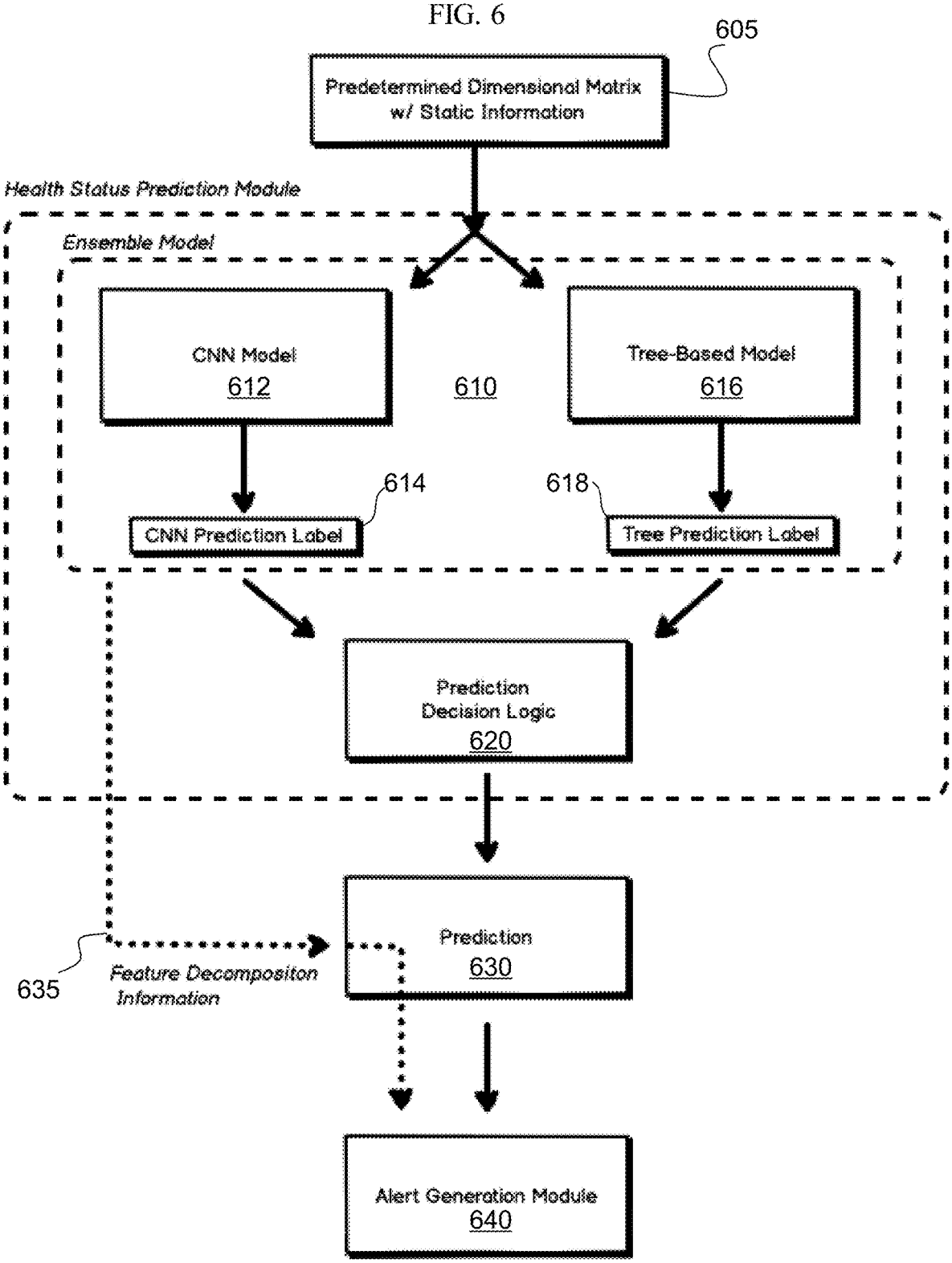

SYSTEMS AND METHODS USING ENSEMBLE MACHINE LEARNING TECHNIQUES FOR FUTURE EVENT DETECTION

BACKGROUND

Systems for assisting healthcare practitioners in monitoring patient health conditions of individual patients are ineffective at providing the timely and accurate detection required to effectively respond to changing health status. This may have devastating results for such patient/s who may die or stop showing progress due to the heavy workload of and inability to monitor health conditions by healthcare practitioners.

SUMMARY

Disclosed herein are platforms, systems, devices, software, and methods for processing and analyzing real-time data to generate predictions of near future events. Machine learning algorithms can be configured for varying levels of aggression to enhance timeliness of the predictions. As disclosed herein, ensemble machine learning techniques combining a plurality of trained models configured with higher and lower aggression levels are used to improve both timeliness and accuracy.

Conventional health monitoring systems record the health data of one or more patients by tracking one or more health parameters through multiple body sensors which are placed on the body of the patient/s or through wearable devices. However, such conventional systems are simplistic and less reactive, wherein monitors track information of the patient/s and generate one or more alarms only if the one or more health parameters are inside or outside of a set limit. Also, frequency of the alarms generated by such conventional systems are ambiguous and there is a high probability of false alarms among other factors, which may lead to incorrect decision making by the healthcare practitioners in case of patient care prioritizing. Moreover, such conventional systems notify the healthcare practitioners only upon deterioration of the health condition of the patient/s with little or no predictive elements, and therefore provides a very limited amount of reaction time to the healthcare practitioners for adequate or appropriate patient care.

In some aspects, disclosed herein is a status monitoring and future event prediction system comprising: a data analytics subsystem comprising: data pre-processing module configured to: receive health data of one or more patients from one or more medical data acquisition devices; and filter the health data to eliminate one or more outliers; a data processing module operatively coupled to the data pre-processing module, wherein the data processing module is configured to: create a predetermined dimensional matrix representative of a plurality of samples obtained from a moving window of the filtered health data representative of the plurality of health parameters of the one or more patients in a predefined interval; and process one or more samples selected from the plurality of samples of the predetermined dimensional matrix based on a predefined condition; and a future event prediction module operatively coupled to the data processing module, wherein the future event prediction module is configured to: label the predetermined dimensional matrix upon processing of the one or more samples using one or more clinical scoring techniques; and predict a future event comprising a health status of the one or more patients in real-time using an ensemble modelling technique upon labelling of the predetermined dimensional matrix, wherein the future event predicted to occur at least a minimum period of time after a time period corresponding to the moving window of filtered health data. In some embodiments, the ensemble modelling technique comprises a first model configured for higher recall than precision and a second model configured for higher precision than recall, and wherein the ensemble modelling technique has a higher combined F1 score than the first model and the second model individually. In some embodiments, the first model comprises a neural network. In some embodiments, the second model comprises a tree model. In some embodiments, the minimum period of time is at least 5 minutes after the time period corresponding to the moving window of filtered health data. In some embodiments, the system further comprises a rule-based decision logic for integrating individual predictions generated by the first model and the second model. In some embodiments, the data analytics subsystem is hosted on a cloud server, a local server, one or more medical data acquisition devices or a combination thereof. In some embodiments, the plurality of health parameters comprises at least one of heart rate, blood oxygen, electrocardiogram, respiratory rate, blood pressure, temperature or a combination thereof. In some embodiments, the one or more outliers comprises at least one of additional movements of the one or more patients, misplacement of one or more sensors, one or more data artefacts, one or more noises or a combination thereof. In some embodiments, the one or more medical data acquisition devices comprises a bedside monitoring device comprising at least one communication medium to receive the plurality of health parameters from one or more sensors and a display interface. In some embodiments, the one or more medical data acquisition devices are configured to: collect health data representative of a plurality of health parameters from the one or more patients through the one or more sensors; and display the health data collected from the one or more patients on the display interface via a predefined icon from a plurality of designated icons. In some embodiments, the predefined condition comprises selection of the one or more samples having the plurality of health parameters more than a predefined threshold value for a predefined time period. In some embodiments, the data processing module is configured to process static information associated with the one or more patients, wherein the static information comprises patient demographics, patient health condition or one or more clinical notes. In some embodiments, the ensemble modelling technique comprises at least one of a dilated causal convolution network, a tree-based gradient boosted technique, a recurrent neural network, a graph neural network, a support vector machine classifier, a logistic regression technique, a k-nearest neighbor classifier, or any combination thereof. In some embodiments, the future event prediction module is configured to implement an online training technique to fine-tune a prediction model corresponding to one or more clinical and operational requirements of an area of implementation or a patient health condition. In some embodiments, the system further comprises an alert generation module operatively coupled to the future event prediction module, wherein the alert generation module is configured to generate one or more predictive alerts for the one or more patients based on prediction of the health status of the one or more patients. In some embodiments, the one or more predictive alerts generated are described with one or more contributing input features using a class activation map technique, wherein the class activation map technique determines the one or more input contributing features responsible for successful prediction of clinical scores in multiclass prediction. In some embodiments, the alert generation module is configured to add hysteresis for providing one or more escalation processes based on a plurality of prediction classes predicted by the future event prediction module. In some embodiments, the alert generation module is configured to: transmit the one or more predictive alerts to one or more corresponding stakeholders for creating awareness associated with the health status of the one or more patients based on the predictive value; and prioritize a list of the one or more patients with a predictive value higher than a predetermined predictive value based on transmission of the one or more predictive alerts. In some embodiments, the system further comprises a communication module configured to send predicted health status of the one or more patients and the one or more predictive alerts to one or more handheld computing devices and one or more handheld electronic devices associated with at least one of the one or more patients or one or more stakeholders associated with the one or more patients, wherein the one or more stakeholders comprises at least one of a caregiver, a nurse, a healthcare practitioner, or any combination thereof.

In some aspects, disclosed herein is a health monitoring system for one or more patients comprising: a health analytics subsystem comprising: a health data processing module configured to: create a predetermined dimensional matrix representative of a plurality of samples obtained from a moving window of filtered health data representative of a plurality of health parameters of the one or more patients in a predefined interval; and process one or more samples selected from the plurality of samples of the predetermined dimensional matrix based on a predefined condition; and a health status prediction module operatively coupled to the health data processing module, wherein the health status prediction module is configured to: label the predetermined dimensional matrix upon processing of the one or more samples using one or more clinical scoring techniques; and predict health status of the one or more patients in real-time using an ensemble modelling technique upon labelling of the predetermined dimensional matrix. In some embodiments, wherein the health analytics subsystem is hosted on a cloud server, a local server, one or more medical data acquisition devices or a combination thereof. In some embodiments, the plurality of health parameters comprises at least one of heart rate, blood oxygen, electrocardiogram, respiratory rate, blood pressure, temperature or a combination thereof. In some embodiments, the health analytics subsystem comprising a health data pre-processing module configured to: receive the health data of the one or more patients from one or more medical data acquisition devices; and filter the health data to eliminate one or more outliers. In some embodiments, the one or more outliers comprises at least one of additional movements of the one or more patients, misplacement of one or more sensors, one or more data artefacts, one or more noises or a combination thereof. In some embodiments, the one or more medical data acquisition devices comprises a bedside monitoring device comprising at least one communication medium to receive the plurality of health parameters from one or more sensors and a display interface. In some embodiments, the one or more medical data acquisition devices are configured to: collect health data representative of a plurality of health parameters from the one or more patients through the one or more sensors; and display the health data collected from the one or more patients on the display interface via a predefined icon from a plurality of designated icons. In some embodiments, the predefined condition comprises selection of the one or more samples having the plurality of health parameters more than a predefined threshold value for a predefined time period. In some embodiments, the health data processing module is configured to process static information associated with the one or more patients, wherein the static information comprises patient demographics, patient health condition or one or more clinical notes. In some embodiments, the ensemble modelling technique comprises at least one of a dilated causal convolution network, a tree-based gradient boosted technique, a recurrent neural network, a graph neural network, a support vector machine classifier, a logistic regression technique, a k-nearest neighbor classifier or a combination thereof. In some embodiments, the health status prediction module is configured to implement an online training technique to fine-tune a prediction model corresponding to one or more clinical and operational requirements of an area of implementation or the patient health condition. In some embodiments, the system further comprises an alert generation module operatively coupled to the health status prediction module, wherein the alert generation module is configured to generate one or more predictive alerts for the one or more patients based on prediction of the health status of the one or more patients. In some embodiments, the one or more predictive alerts generated are described with one or more contributing input features using a class activation map technique, wherein the class activation map technique determines the one or more input contributing features responsible for successful prediction of clinical scores in multiclass prediction. In some embodiments, the alert generation module is configured to add hysteresis for providing one or more escalation processes based on a plurality of prediction classes predicted by the health status prediction module. In some embodiments, the alert generation module is configured to: transmit the one or more predictive alerts to one or more corresponding stakeholders for creating awareness associated with the health status of the one or more patients based on the predictive value; and prioritize a list of the one or more patients with a predictive value higher than a predetermined predictive value based on transmission of the one or more predictive alerts. In some embodiments, the alert generation module is configured to receive a feedback response corresponding to the one or more predictive alerts from the one or more stakeholders. In some embodiments, the system comprises a communication module configured to send predicted health status of the one or more patients and the one or more predictive alerts to one or more handheld computing devices and one or more handheld electronic devices associated with at least one of the one or more patients and one or more stakeholders associated with the one or more patients respectively, wherein the one or more stakeholders comprises at least one of one or more caregivers, a nurse, a healthcare practitioner or a combination thereof.

In some aspects, disclosed herein is a method comprising: creating, by a health data processing module, a predetermined dimensional matrix representative of a plurality of samples obtained from a moving window of filtered health data representative of a plurality of health parameters of one or more patients in a predefined interval; processing, by the health data processing module, one or more samples selected from the plurality of samples of the predetermined dimensional matrix based on a predefined condition; labelling, by a health status prediction module of the health analytics subsystem, the predetermined dimensional matrix upon processing of the one or more samples using one or more clinical deterioration scoring techniques; and predicting, by the health status prediction module, health status of the one or more patients in real-time using an ensemble modelling technique upon labelling of the predetermined dimensional matrix. In some embodiments, the method further comprising generating, by an alert generation module, one or more predictive alerts for the one or more patients based on prediction of the health status of the one or more patients. In some embodiments, the method further comprises: transmitting, by the alert generation module, the one or more predictive alerts to one or more corresponding stakeholders for creating awareness associated with the health status of the one or more patients based on the predictive value; and prioritizing, by the alert generation module, a list of the one or more patients with a predictive value higher than a predetermined predictive value based on transmission of the one or more predictive alerts.

In some aspects, provided herein is a health monitoring system for one or more patients comprising: a health data processing module configured to: generate a multi-dimensional matrix comprising a plurality of samples obtained from a moving window of health data for one or more patients; and process one or more samples selected from the plurality of samples of the multi-dimensional matrix based on a predefined condition; and a health status prediction module configured to: label the multi-dimensional matrix upon processing of the one or more samples using one or more clinical scoring techniques; and predict health status of the one or more patients in real-time using an ensemble modelling technique based on the label of the dimensional matrix. In some embodiments, the health data processing module is implemented through a health analytics subsystem hosted on a cloud server, a local server, one or more medical data acquisition devices, or a combination thereof. In some embodiments, the health analytics subsystem comprises a health data pre-processing module configured to: receive the health data for the one or more patients from one or more medical data acquisition devices; and filter the health data to eliminate one or more outliers. In some embodiments, the one or more outliers comprises at least one of additional movements of the patient, misplacement of one or more sensors, one or more data artifacts, or one or more noises. In some embodiments, the health data corresponds to a plurality of health parameters comprising at least one of heart rate, blood oxygen, electrocardiogram, respiratory rate, blood pressure, or temperature. In some embodiments, the health data is representative of a plurality of health parameters of the patient collected using one or more medical data acquisition devices. In some embodiments, the one or more medical data acquisition devices comprises a bedside monitoring device comprising a display interface and at least one communication medium to receive the plurality of health parameters from one or more sensors. In some embodiments, the one or more medical data acquisition devices are configured to: collect the health data representative of the plurality of health parameters from the one or more patients through the one or more sensors; and display the health data collected from the one or more patients on the display interface via a predefined icon from a plurality of designated icons. In some embodiments, the predefined condition comprises selection of the one or more samples having the plurality of health parameters more than a predefined threshold value for a predefined time period. In some embodiments, the health data comprises static information associated with the one or more patients. In some embodiments, the static information comprises at least one of patient demographics, patient health condition, or one or more clinical notes. In some embodiments, the health data processing module is configured to process the static information associated with the one or more patients. In some embodiments, the ensemble modelling technique comprises a plurality of predictive models generated using machine learning. In some embodiments, the plurality of predictive models comprises a convolution neural network (CNN) and a tree-based model. In some embodiments, the ensemble modelling technique comprises a decision logic configured to integrate outputs of the plurality of predictive models in order to predict the health status of the one or more patients. In some embodiments, the ensemble modelling technique comprises at least one of a dilated causal convolution network, a tree-based gradient boosted technique, a recurrent neural network, a graph neural network, a support vector machine classifier, a logistic regression technique, or a k-nearest neighbor classifier. In some embodiments, the health status predicted using the ensemble modelling technique is a prediction of a future health status or change in health status. In some embodiments, the future health status or change in health status is predicted at least 15 minutes in advance of the future health status or change in health status. In some embodiments, the health status predicted using the ensemble modelling technique has an AUC of at least 0.8. In some embodiments, the health status prediction module is configured to implement an online training technique to fine-tune a prediction model of the ensemble modelling technique based on one or more clinical or operational requirements of an area of implementation or the patient health status. In some embodiments, further comprises an alert generation module operatively coupled to the health status prediction module, wherein the alert generation module is configured to generate one or more predictive alerts for the one or more patients based on prediction of the health status of the one or more patients. In some embodiments, the one or more predictive alerts comprise an indication or description of one or more contributing input features determined using a feature decomposition technique. In some embodiments, the feature decomposition technique comprises a class activation map technique, wherein the class activation map technique determines the one or more input contributing features responsible for successful prediction of clinical scores in multiclass prediction. In some embodiments, the alert generation module is configured to add hysteresis for providing one or more escalation processes based on a plurality of prediction classes predicted by the health status prediction module. In some embodiments, the alert generation module is configured to: transmit the one or more predictive alerts to one or more corresponding stakeholders for creating awareness associated with the health status of the one or more patients based on a predictive value corresponding to the health status predicted using the ensemble modelling technique; and prioritize a list of the one or more patients with a predictive value higher than a predetermined predictive value based on transmission of the one or more predictive alerts. In some embodiments, the alert generation module is configured to receive a feedback response corresponding to the one or more predictive alerts from the one or more stakeholders. In some embodiments, the system comprises a communication module configured to send the predicted health status of the one or more patients and the one or more predictive alerts to one or more handheld computing devices or one or more handheld electronic devices associated with at least one of the one or more patients or one or more stakeholders associated with the one or more patients. In some embodiments, the one or more stakeholders comprises at least one of a caregiver, a nurse, or a healthcare practitioner.

In some aspects, provided herein is a method comprising: generating, by a health data processing module, a multi-dimensional matrix comprising a plurality of samples obtained from a moving window of health data for one or more patients; processing, by the health data processing module, one or more samples selected from the plurality of samples of the multi-dimensional matrix based on a pre-defined condition; labeling, by a health status prediction module, the multi-dimensional matrix upon processing of the one or more samples using one or more clinical scoring techniques; and predicting, by a health status prediction module, health status of the one or more patients in real-time using an ensemble modelling technique based on the label of the dimensional matrix. In some embodiments, the health data processing module is implemented through a health analytics subsystem hosted on a cloud server, a local server, one or more medical data acquisition devices, or a combination thereof. In some embodiments, the health analytics subsystem comprises a health data pre-processing module configured to: receive the health data for the one or more patients from one or more medical data acquisition devices; and filter the health data to eliminate one or more outliers. In some embodiments, the one or more outliers comprises at least one of additional movements of the patient, misplacement of one or more sensors, one or more data artifacts, or one or more noises. In some embodiments, the health data corresponds to a plurality of health parameters comprising at least one of heart rate, blood oxygen, electrocardiogram, respiratory rate, blood pressure, or temperature. In some embodiments, the health data is representative of a plurality of health parameters of the patient collected using one or more medical data acquisition devices. In some embodiments, the one or more medical data acquisition devices comprises a bedside monitoring device comprising a display interface and at least one communication medium to receive the plurality of health parameters from one or more sensors. In some embodiments, the one or more medical data acquisition devices are configured to: collect the health data representative of the plurality of health parameters from the one or more patients through the one or more sensors; and display the health data collected from the one or more patients on the display interface via a predefined icon from a plurality of designated icons. In some embodiments, the predefined condition comprises selection of the one or more samples having the plurality of health parameters more than a predefined threshold value for a predefined time period. In some embodiments, the health data comprises static information associated with the one or more patients. In some embodiments, the static information comprises at least one of patient demographics, patient health condition, or one or more clinical notes. In some embodiments, the health data processing module is configured to process the static information associated with the one or more patients. In some embodiments, the ensemble modelling technique comprises a plurality of predictive models generated using machine learning. In some embodiments, the plurality of predictive models comprises a convolution neural network (CNN) and a tree-based model. In some embodiments, the ensemble modelling technique comprises a decision logic configured to integrate outputs of the plurality of predictive models in order to predict the health status of the one or more patients. In some embodiments, the ensemble modelling technique comprises at least one of a dilated causal convolution network, a tree-based gradient boosted technique, a recurrent neural network, a graph neural network, a support vector machine classifier, a logistic regression technique, or a k-nearest neighbor classifier. In some embodiments, the health status predicted using the ensemble modelling technique is a prediction of a future health status or change in health status. In some embodiments, the future health status or change in health status is predicted at least 15 minutes in advance of the future health status or change in health status. In some embodiments, the health status predicted using the ensemble modelling technique has an AUC of at least 0.8. In some embodiments, the health status prediction module is configured to implement an online training technique to fine-tune a prediction model of the ensemble modelling technique based on one or more clinical or operational requirements of an area of implementation or the patient health status. In some embodiments, the method further comprises using an alert generation module operatively coupled to the health status prediction module, wherein the alert generation module is configured to generate one or more predictive alerts for the one or more patients based on prediction of the health status of the one or more patients. In some embodiments, the one or more predictive alerts comprise an indication or description of one or more contributing input features determined using a feature decomposition technique. In some embodiments, the feature decomposition technique comprises a class activation map technique, wherein the class activation map technique determines the one or more input contributing features responsible for successful prediction of clinical scores in multiclass prediction. In some embodiments, the alert generation module is configured to add hysteresis for providing one or more escalation processes based on a plurality of prediction classes predicted by the health status prediction module. In some embodiments, the alert generation module is configured to: transmit the one or more predictive alerts to one or more corresponding stakeholders for creating awareness associated with the health status of the one or more patients based on a predictive value corresponding to the health status predicted using the ensemble modelling technique; and prioritize a list of the one or more patients with a predictive value higher than a predetermined predictive value based on transmission of the one or more predictive alerts. In some embodiments, the alert generation module is configured to receive a feedback response corresponding to the one or more predictive alerts from the one or more stakeholders. In some embodiments, the system comprises a communication module configured to send the predicted health status of the one or more patients and the one or more predictive alerts to one or more handheld computing devices or one or more handheld electronic devices associated with at least one of the one or more patients or one or more stakeholders associated with the one or more patients. In some embodiments, the one or more stakeholders comprises at least one of a caregiver, a nurse, or a healthcare practitioner.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 is a flow chart representing an ensemble modelling method of a health monitoring system in accordance with some embodiments of the present disclosure.

DETAILED DESCRIPTION

Figure 1:
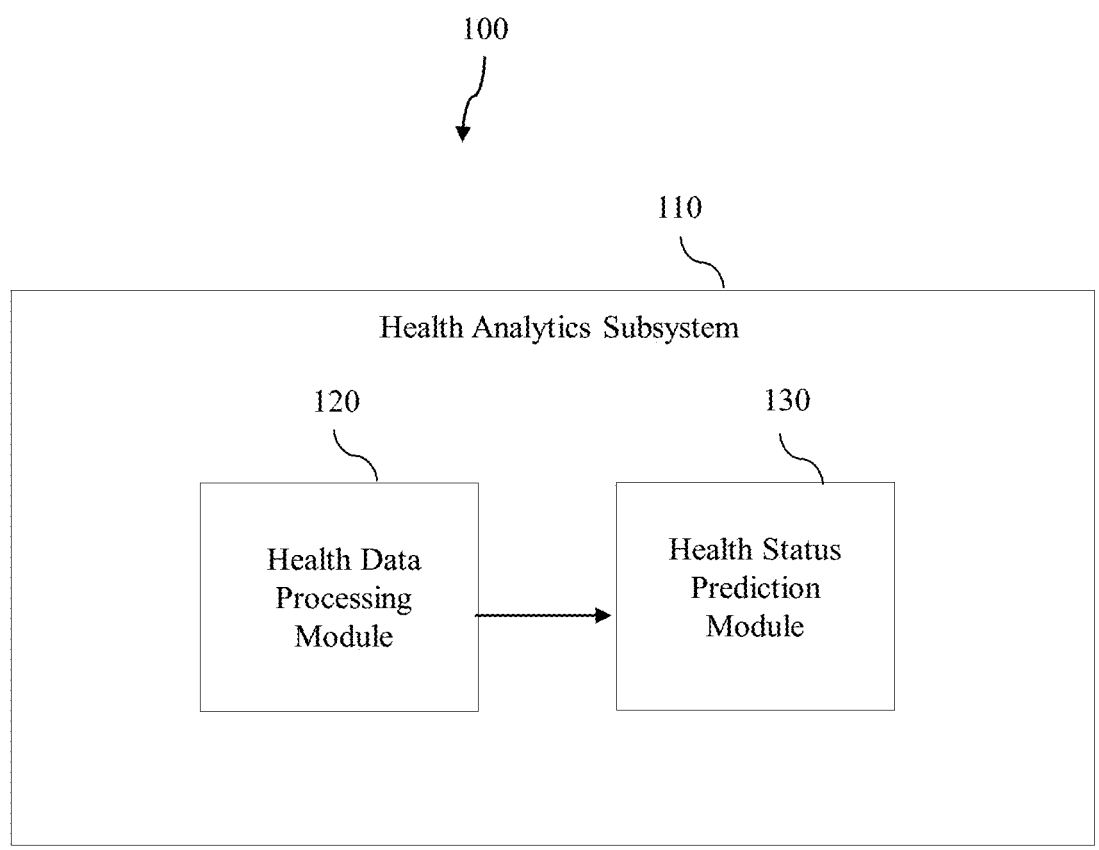
FIG. 1 is a block diagram of a health monitoring system for one or more patients in accordance with some embodiments of the present disclosure.

Disclosed herein are platforms, systems, devices, software, and methods for processing and analyzing real-time data to generate predictions of near future events. Machine learning algorithms can be configured for varying levels of aggression to enhance timeliness of the predictions. In some cases, ensemble machine learning techniques combining a plurality of trained models configured with higher and lower aggression levels are used to improve both timeliness and accuracy.

In some embodiments, disclosed herein are healthcare monitoring systems and methods that provide improved patient monitoring and tracking of changes in health condition.

In accordance with some embodiments of the present disclosure, a health monitoring system for one or more patients is disclosed. The system may include a health analytics subsystem hosted on a server. The health data analytics subsystem may include a health data processing module to create a predetermined dimensional matrix representative of a plurality of health parameters of the one or more patients and a multiple of samples obtained from a moving window of filtered health data in a predefined interval. The health data processing module may process one or more samples selected from the multiple of samples of the predetermined dimensional matrix based on a predefined condition. The health data analytics subsystem may also include a health status prediction module. The health status prediction module may label the predetermined dimensional matrix upon processing of the one or more samples using one or more clinical deterioration scoring techniques. The health status prediction module may also predict health status of the one or more patients in real-time using an ensemble modelling technique upon labelling of the predetermined dimensional matrix.

In accordance with some embodiments of the present disclosure, a method to operate the health monitoring system for one or more patients is disclosed. The method may include creating a predetermined dimensional matrix representative of a multiple of samples obtained from a moving window of filtered health data representative of a plurality of health parameters of the one or more patients in a predefined interval. The method may also include processing one or more samples selected from the multiple of samples of the predetermined dimensional matrix based on a predefined condition. In some embodiments, the method includes labelling the predetermined dimensional matrix upon processing of the one or more samples using one or more clinical deterioration scoring techniques. The method may also include predicting health status of the one or more patients in real-time using an ensemble modelling technique upon labelling of the predetermined dimensional matrix.

Embodiments of the present disclosure relate to a health monitoring system for one or more patients and a method to operate the same in order to address the aforementioned issues. The system may include a health analytics subsystem hosted on a server. The health analytics subsystem may include a health data processing module to create a predetermined dimensional matrix representative of a multiple of samples obtained from a moving window of filtered health data representative of a plurality of health parameters of the one or more patients in a predefined interval. The health data processing module may also process one or more samples selected from the multiple of samples of the predetermined dimensional matrix based on a predefined condition. In some embodiments, the health data analytics subsystem also includes a health status prediction module. The health status prediction module labels the predetermined dimensional matrix upon processing of the one or more samples using one or more clinical deterioration scoring techniques. The health status prediction module may also predict a health status of the one or more patients in real-time using an ensemble modelling technique upon labelling of the predetermined dimensional matrix.

FIG. 1 is a block diagram of a health monitoring system (100) for one or more patients in accordance with some embodiments of the present disclosure. In some embodiments, the system (100) may include a health analytics subsystem (110). The health analytics subsystem (110) may be hosted on a cloud server, a local server, one or more medical data acquisition subsystem or a combination thereof. The health analytics subsystem may collect at least one of real-time patient demographic information, disease state information, one or more customizable health metrics or a combination thereof. In some embodiments, the health analytics subsystem (110) includes a health data pre-processing module to receive health data representative of multiple health parameters of the one or more patients from one or more medical data acquisition devices in real-time. The multiple health parameters may comprise at least one of a heart rate, a blood oxygen level, electrical signals produced by a heart (e.g., electrocardiogram), a respiratory rate, a blood pressure, a body temperature, or a combination thereof. The multiple health parameters may also include multiple derivative health parameters derived from the multiple health parameters.

Medical acquisition devices may collect data representative of multiple health parameters in a non-invasive manner. In some embodiments, a heart rate is obtained by a stethoscope or electrocardiogram. In some embodiments, electric signals produced by the heart are recorded by an electrocardiogram. An electrocardiogram may use electrodes placed near the heart to detect electrical signals produced by a cardiac cycle. An electrocardiogram may produce, display, and or record the measured voltages produced by the heart as a function of time.

In some embodiments, a blood oxygen level is measured by an electronic oximeter. Said oximeter may measure peripheral oxygen saturation, arterial oxygen saturation, or a combination thereof. The oximeter may measure a blood oxygen level using a transmissive pulse oximetry technique and be attached to a patient at a fingertip, earlobe, foot, wrist, or any suitable area of a patient's body. The oximeter may measure a blood oxygen level using a reflectance pulse oximetry technique and be attached to any suitable area of a patient's body. The application mode (i.e. transmissive pulse oximetry or reflectance pulse oximetry) may be chosen based on a patient's condition. For example, a patient anesthetized for endotracheal intubation may have an oximeter placed on the forehead to monitor for sporadic oxygen levels using a reflectance pulse oximetry technique.

In some embodiments, a blood pressure is monitored by a sphygmomanometer. In some embodiments, blood pressure is monitored by an arterial catheter. In some embodiments, a body temperature is monitored by a thermometer. The thermometer may be a wearable digital thermometer.

In some embodiments, the one or more medical acquisition devices include a bedside monitoring device which includes at least one communication medium to receive the multiple health parameters from one or more sensors and a display interface for displaying at least one of the multiple health parameters in the real-time. As used herein, the term 'communication medium' may be defined as a channel which enables communication between the data collected from the one or more patients through the one or more sensors. The at least one communication medium may include a wired communication medium, a wireless communication medium or a combination thereof. In some embodiments, the one or more medical data acquisition devices collect health data representative of the multiple health parameters from the one or more patients through the one or more sensors. The one or more medical data acquisition devices may also include display interfaces to display real-time status of the health data collected from the one or more patients.

In some embodiments, the system (100) also includes a handheld computing device connected with the one or more medical data acquisition devices for integration of the health data representative of the multiple health parameters collected from the one or more patients. The handheld computing device may include, but not be limited to, a tablet, a personal digital assistant (PDA), a mobile phone, and the like, associated with the one or more patients and one or more stakeholders associated with the one or more patients. The handheld computing device may enable configuration of patient specific settings. In some embodiments, the handheld computing device communicates with the health analytics subsystem via a wireless communication network. The wireless communication network may include a cellular network, a wireless fidelity network, a Bluetooth technology and the like. The health data pre-processing module (120) may also filter the health data to eliminate one or more outliers. In some embodiments, the one or more outliers includes at least one of additional movements of the one or more patients, misplacement of one or more sensors, one or more data artefacts, one or more noises or a combination thereof.

The health analytics subsystem (110) may also include a health data processing module (120) to create a predetermined dimensional matrix representative of multiple of samples obtained from a moving window of filtered health data in a predefined interval. The predefined interval can be configured based on the type(s) of health status being monitored. For example, certain conditions or deteriorations in health status may progress rapidly and require a shorter duration window to be detected in time to provide early warning to healthcare professionals. In other cases, the health status change may be a more gradual progression which may require a longer duration window to be accurately detected. In some embodiments, the systems and methods disclosed herein are configured to monitor multiple health statuses using predefined intervals that are customized or specific to each respective health status. In some embodiments, at least 2, 3, 4, or 5 health statuses are monitored simultaneously. In some embodiments, a given predefined interval can have a duration of at least 1, 2, 3, 4, 5, 10, 15, 20, 30, 40, 50, 60, 70, 80, 90, 110, or 120 minutes, and/or no more than 1, 2, 3, 4, 5, 10, 15, 20, 30, 40, 50, 60, 70, 80, 90, 110, or 120 minutes. As an illustrative example, the predefined time interval includes a two-hour duration. In some embodiments, the duration of the predetermined time interval defines the column height of the matrix. In some embodiments, the predetermined time interval is adapted based on performance monitored over time. In some embodiments, a machine learning algorithm or artificial intelligence changes the predetermined time interval. In some embodiments, the time interval is changed or updated based on new information, for example, new data and outcomes are used to adjust the time interval to provide greater accuracy. In some embodiments, the predetermined dimensional matrix includes a 2D matrix. The moving window may move at any interval of the filtered health data flow. One dimension of the matrix can be the time interval. For example, a 2D matrix may include multiple columns with each column including sensor data for a particular parameter (e.g., heart rate, blood pressure, temperature, etc.), while the rows correspond to time units. In this example, a longer time interval means a greater number of rows. Since, the filtered health data may flow at different rates, the health data processing module may enable either down-sampling or up-sampling to ensure the 2D matrix is sufficiently full. As an illustrative example, a 30 minute time interval may have sensor data for heart rate that occur every 10 seconds but temperature data that occur every 30 seconds. Thus, this discrepancy in sampling rate of the sensors can be normalized by pre-processing the sensor data, for example, up-sampling the slower sensor data and/or down-sampling the faster sensor data.

The health data processing module (120) may also process one or more samples selected from the multiple of samples of the predetermined dimensional matrix based on a predefined condition or requirement in real-time. In some embodiments, the predefined condition or requirement includes selection of the one or more samples having the multiple health parameters that pass beyond a predefined threshold value for a predefined time period. As an illustrative example, the analysis of data for 3 different types of sensor data may be determined to be unreliable if data is unavailable for 20% or more of the predefined duration or time period for at least 2 of the sensor parameters. Accordingly, in some embodiments, during processing of the health data, further processing and/or analysis is halted or paused until more data is available and/or a warning or result is not generated or provided until the threshold value or condition is satisfied. In some embodiments, the predefined condition includes selection of the one or more samples which have more than 3 health parameters which pass beyond a predefined threshold value for 80% of the predefined duration selected. In some embodiments, the predefined threshold is adjusted over time. In some embodiments, the matrix is filled after data is down-sampled. In some embodiments, the matrix is filled after data is up-sampled. In some embodiments, the predefined threshold is adjusted based on performance monitored over time. In some embodiments, a machine learning algorithm or artificial intelligence adjusts the predefined threshold time interval. Each sample from the one or more patients, may be treated independently for training of the model, as one patient may have multiple samples. When no values are available or a not a number (NaN) values are obtained, such spaces may be replaced by (−1 or 0) for a convolutional neural network (CNN) to ensure the data is not considered.

A tree-based technique may handle non-zero values. The health data processing module may also implement confidence improving strategies to ensure that the scores of the multiple of samples lead to a true positive based on at least one of hysteresis, low pass filtering, rules determined from clinical knowledge of human physiology or a combination thereof. In some embodiments, the health data processing module also normalizes the predetermined dimensional matrix of health parameters in a common range with respect to entire data available and thereby remove eliminate local maximums and local minimums. In some embodiments, the health data processing module (120) also processes static information associated with the one or more patients as fixed data across the predetermined dimensional matrix in real-time, wherein the static information may include patient demographics, patient health condition, one or more clinical notes and the like. Patient demographics may include, health conditions, and clinical notes may include age, gender, ethnicity, body mass index (BMI), medical history, blood type, allergies, pre-existing conditions, comorbidities, surgical history, major diagnoses, and the like. Such fixed data can be analyzed as features alongside the dimensional matrix by a model, for example, a convolutional neural network. Unlike the dynamic sensor data, static data may not be processed using a moving multi-dimensional matrix since it would not change over a short time scale.

In some embodiments, the predefined condition includes selection of the one or more samples which have one health parameter which passes beyond a predefined threshold value to 10 health parameters which pass beyond a predefined threshold value.

In some embodiments, the predefined condition includes selection of the one or more samples which have 1 health parameter which passes beyond a predefined threshold value to 2 health parameters which pass beyond a predefined threshold value, 1 health parameter which passes beyond a predefined threshold value to 3 health parameters which pass beyond a predefined threshold value, 1 health parameter which passes beyond a predefined threshold value to 4 health parameters which pass beyond a predefined threshold value, 1 health parameter which passes beyond a predefined threshold value to 5 health parameters which pass beyond a predefined threshold value, 1 health parameter which passes beyond a predefined threshold value to 6 health parameters which pass beyond a predefined threshold value, 1 health parameter which passes beyond a predefined threshold value to 10 health parameters which pass beyond a predefined threshold value, 2 health parameters which pass beyond a predefined threshold value to 3 health parameters which pass beyond a predefined threshold value, 2 health parameters which pass beyond a predefined threshold value to 4 health parameters which pass beyond a predefined threshold value, 2 health parameters which pass beyond a predefined threshold value to 5 health parameters which pass beyond a predefined threshold value, 2 health parameters which pass beyond a predefined threshold value to 6 health parameters which pass beyond a predefined threshold value, 2 health parameters which pass beyond a predefined threshold value to 10 health parameters which pass beyond a predefined threshold value, 3 health parameters which pass beyond a predefined threshold value to 4 health parameters which pass beyond a predefined threshold value, 3 health parameters which pass beyond a predefined threshold value to 5 health parameters which pass beyond a predefined threshold value, 3 health parameters which pass beyond a predefined threshold value to 6 health parameters which pass beyond a predefined threshold value, 3 health parameters which pass beyond a predefined threshold value to 10 health parameters which pass beyond a predefined threshold value, 4 health parameters which pass beyond a predefined threshold value to 5 health parameters which pass beyond a predefined threshold value, 4 health parameters which pass beyond a predefined threshold value to 6 health parameters which pass beyond a predefined threshold value, 4 health parameters which pass beyond a predefined threshold value to 10 health parameters which pass beyond a predefined threshold value, 5 health parameters which pass beyond a predefined threshold value to 6 health parameters which pass beyond a predefined threshold value, 5 health parameters which pass beyond a predefined threshold value to 10 health parameters which pass beyond a predefined threshold value, or 6 health parameters which pass beyond a predefined threshold value to 10 health parameters which pass beyond a predefined threshold value. In some embodiments, the predefined condition includes selection of the one or more samples which have 1 health parameter which passes beyond a predefined threshold value, 2 health parameters which pass beyond a predefined threshold value, 3 health parameters which pass beyond a predefined threshold value, 4 health parameters which pass beyond a predefined threshold value, 5 health parameters which pass beyond a predefined threshold value, 6 health parameters which pass beyond a predefined threshold value, or 10 health parameters which pass beyond a predefined threshold value. In some embodiments, the predefined condition includes selection of the one or more samples which have at least 1 health parameter which passes beyond a predefined threshold value, 2 health parameters which pass beyond a predefined threshold value, 3 health parameters which pass beyond a predefined threshold value, 4 health parameters which pass beyond a predefined threshold value, 5 health parameters which pass beyond a predefined threshold value, or 6 health parameters which pass beyond a predefined threshold value. In some embodiments, the predefined condition includes selection of the one or more samples which have at most 2 health parameters which pass beyond a predefined threshold value, 3 health parameters which pass beyond a predefined threshold value, 4 health parameters which pass beyond a predefined threshold value, 5 health parameters which pass beyond a predefined threshold value, 6 health parameters which pass beyond a predefined threshold value, or 10 health parameters which pass beyond a predefined threshold value.

In some embodiments, the predefined condition includes selection of the one or more samples which have one or more health parameters which pass beyond a predefined threshold value for at least about 65 percent of the predefined duration selected. In some embodiments, the predefined condition includes selection of the one or more samples which have one or more health parameters which pass beyond a predefined threshold value for at least about 65 percent of the predefined duration selected, at least about 70 percent of the predefined duration selected, at least about 75 percent of the predefined duration selected, at least about 80 percent of the predefined duration selected, at least about 85 percent of the predefined duration selected, at least about 90 percent of the predefined duration selected, or at least about 95 percent of the predefined duration selected.

In some embodiments, the health analytics subsystem (110) also includes a health status prediction module (130). The health status prediction module (130) may label the predetermined dimensional matrix upon processing of the one or more samples in the real-time using one or more clinical deterioration scoring techniques. In some embodiments, the predetermined dimensional matrix includes unlabeled health data. The unlabeled data of the predetermined dimensional matrix may be labelled using a clustering technique. Clustering techniques may include portioning method, hierarchical clustering, fuzzy clustering, density-based clustering, model-based clustering, and the like, as disclosed herein. In some embodiments, the one or more clinical deterioration scoring techniques include at least one of a modified early warning scoring technique, universal vital assessment technique, a quick sequential organ failure assessment technique (qSOFA), or a combination thereof, as disclosed herein. These clinical deterioration scoring techniques are typically used as static techniques in clinical literature for converting static vital signs into a static holistic score. The systems and methods disclosed herein can apply these techniques to the health data, for example, data within the multi-dimensional matrix for various sensor parameters. A challenge with the conventional use of these static scoring techniques is that once the score is high enough to reach a threshold for deterioration, it may be already too late. Accordingly, the systems and methods disclosed herein can apply this scoring to the multi-dimensional matrix of health data to identify health status changes ahead of time for early warning detection. In other words, the systems and methods disclosed herein can predict when the clinically agreed scores will be high or low in the near future (e.g., patient is predicted to get worse or stabilize within 30 minutes). The algorithm can be trained to make such predictions using a multi-dimensional matrix. For example, a 2-hour duration interval is used for heart rate, blood pressure, and body temperature sensor readings. As the time passes, the data within the matrix dynamically updates as older readings falling outside the past 2 hours are removed from the matrix and new readings are added to the matrix. The matrix can be evaluated using a clinical deterioration scoring technique over time until a score indicating deterioration is determined. At this point, the conventional analysis is too late because the health status has already deteriorated. However, this information can be used to look back in time to an earlier duration, e.g., 30 minutes before. The matrix data from this earlier duration can be labelled as corresponding to a later deterioration in health status. A training data set comprising matrix data labelled as indicating of the presence or absence of later deterioration can then be used to train a model (e.g., CNN) to differentiate between later deterioration based on earlier matrix data. The extent to which the model is configured to predict health status changes ahead of time can vary. In some embodiments, the model(s) is configured to predict a future health status change that is at least 1, 2, 3, 4, 5, 10, 15, 20, 25, 30, 35, 40, 45, 50, 55, or 60 minutes ahead of time. In some embodiments, the future event (e.g., health status change) is detected about 10 to 30 minutes ahead of time. In some embodiments, the future event is detected about 15 to 25 minutes ahead of time. In some embodiments, the future event is detected about 20 minutes ahead of time.

Clinical deterioration scoring techniques may comprise assigning a score to a patient's health condition based on one or more health parameters. Health parameters may be obtained from one or more medical data acquisition devices. The medical data acquisition device may obtain health parameter measurements in real-time. In some embodiments, the health parameters include at least one of a heart rate, a blood, oxygen level, electrical signals produced by a heart, a respiratory rate, a blood pressure, a body temperature, or a combination thereof. Scoring techniques may also consider patient demographics, patient health condition, one or more clinical notes and the like. Patient demographics may include, health conditions, and clinical notes may include age, gender, ethnicity, body mass index (BMI), medical history, blood type, allergies, pre-existing conditions, comorbidities, surgical history, major diagnoses, and the like.

In some embodiments, the health status prediction module (130) also predicts health status of the one or more patients in real-time using an ensemble modelling technique after labelling of the predetermined dimensional matrix, as disclosed herein. In some embodiment, the health status includes a progress in health condition of the one or more patients. In some embodiments, the progress in the health condition includes, but is not limited to, stability in health condition of the one or more patients, discharge notification of the one or more patients from hospitals, and the like. In some embodiments, the health status includes a health deterioration of the one or more patients. In some embodiments, the ensemble modelling technique includes at least one of a dilated causal convolution network, a tree-based gradient boosted technique, a recurrent neural network, a graph neural network, a support vector machine classifier, a logistic regression technique, a k-nearest neighbor classifier, or a combination thereof, as disclosed herein. In some embodiments, the dilated causal convolution networks are utilized for aggressive and fast prediction of the health status of the one or more patients, as disclosed herein. In some embodiments, the model is activated to generate predictions after the pre-determined time interval has elapsed. The system may continuously analyze data in real-time to generate predictions. In some embodiments, the tree-based gradient boosted technique may be utilized for reducing one or more false positives. In some embodiments, the ensemble modelling technique balances the prediction of the health status and also removes false alarms. The ensemble modelling technique may integrate multiple clinical labels and learn from such labels to maximize absorption of the clinical deterioration scoring technique for prediction of the health status of the one or more patients.

A diagram illustrating an ensemble modelling technique is depicted by FIG. 6, according to some embodiments. In some embodiments, the matrix 605 sent to the ensemble model 610 contains both the health parameters and the static information. The static information may be appended as columns of the matrix. This new, complete matrix can be sent to the ensemble model for analysis. The ensemble model can include two or more predictive models, each configured to generate a prediction (e.g., a predicted health status or change thereof for a patient).

In some embodiments, the ensemble method 610 receives a predetermined matrix of data which includes health data captured at a predetermined frequency for a predetermined length of time. This matrix can provide a holistic picture of the patient's condition which is analyzed by the model to make a proactive alert of changes to health status to the clinical teams. The proactive alert can predict a future health status or a change in health status. In some embodiments, the prediction is generated at least 1, 2, 3, 4, 5, 10, 15, 20, 25, 30, 40, 50, 60, 70, 80, 90, 100, 110, or at least 120 minutes ahead of the predicted health status or change in health status, thereby allowing for a proactive alert to be provided to the patient, a stakeholder, a healthcare practitioner, a clinical team, or other relevant party.

In some embodiments, an ensemble alerting technique is utilized to solve a key problem in proactive alerting by balancing the timeliness of the alert to false positives. More time spent collecting data to lower the chances of false positives may lower the proactivity of the alert, but less time collecting data may increase the chance of producing false alerts or false positives. In some embodiments, the ensemble method utilizes multiple machine learning and/or AI models to achieve a balanced approach by pairing models that have a different prediction representation. Various performance metrics can be used to validate or test a given machine learning or AI model, for example, sensitivity/recall/true positive rate, specificity/selectivity/true negative rate, precision/positive predictive value, and/or negative predictive value.

The ensemble machine learning technique can incorporate a plurality of machine learning models, for example, at least two, three, four, or five machine learning models that are used together for a generating particular type of prediction. Each model can be trained to a certain level of aggression. In some embodiments, a first model used in the ensemble is trained to be more aggressive (higher recall; also referred to as sensitivity) in order to catch more of the true positives, which tends to involve a trade-off of more false positives (lower precision; also referred to as positive predictive value). In some embodiments, a second model used in the ensemble is trained to be more precise in order to reduce the number of false positives, which tends to involve a trade-off of catching fewer true positives (lower recall). The models can be configured for greater or lower aggression/precision during training. In some cases, a more or less aggressive model can be trained by setting a constraint for a minimum recall or precision and then tuning the model according to various parameters to maximize overall performance while meeting the minimum recall or precision constraint. For example, a neural network can be configured by adjusting the neurons per layer, activation functions between neurons and/or layers, number of layers, pooling of layers, and other suitable parameters. As another example, a tree model can be configured by adjusting the number of trees being used, the number of features to be used in each branch of the tree, the depth for each tree and the depth of each branch, and other suitable parameters.

In some embodiments, the ensemble modelling technique comprises training a first model and a second model in which the first model has a higher recall and a lower precision than the second model. Performance metrics such as recall, precision, and F1 score can be assessed by testing the model(s) against test data (e.g., data withheld from training data used to generate the trained model(s)). In some cases, the ensemble modelling technique combines the models such that predictions have statistically equal or higher recall and precision compared to each of the individual models. In some embodiments, the ensemble modelling approach generates predictions that are statistically higher in at least one of precision or recall compared to any single model that contributes to the ensemble prediction. In some embodiments, the ensemble modelling technique generates an ensemble prediction that has a higher F1 score than can be achieved using the individual non-ensemble models. In some embodiments, the ensemble model prediction has a statistically higher recall than any single model that contributes to the ensemble by at least 0.01, 0.02, 0.03, 0.04, or 0.05. In some embodiments, the ensemble model prediction has a statistically higher precision than any single model that contributes to the ensemble by at least 0.01, 0.02, 0.03, 0.04, or 0.05. As used herein, the statistical comparisons of performance metrics such as precision and recall can be generated using test/validation data set withheld from the training data.

Combining individual models in an ensemble approach is not guaranteed to improve performance. Surprisingly, it was discovered that an ensemble approach that specifically includes one or more models trained for greater aggression and one or more models trained for greater precision resulted in higher overall combined scores than the individual models could achieve alone. Accordingly, present disclosure demonstrated that the fundamental problem of precision and recall being a trade-off could be compensated for using ensemble modelling. This is of critical importance within the unique context of detecting or predicting near future events (e.g., health status change) because a highly accurate model is useless if it cannot predict sufficiently far into the future to give healthcare practitioners enough forewarning to prepare for the event before it occurs. As an illustrative example, if an additional 5 minutes of data is needed to detect a future event, then that reduces the timeliness by those 5 minutes, which may be too late. Accordingly, an important advantage provided by the ensemble techniques disclosed herein is the ability to maximize both precision and recall for a higher F1 score.

In addition, given that the performance metrics can be improved to 0.90 or higher using ensemble, this allows for optimization of other aspects of the system aside from accuracy. For example, the system can be optimized for speed to enhance real-time prediction/detection, integrating more data, and other factors to increase efficiency.

In some embodiments, the more aggressive model has a higher recall than precision. In some embodiments, the less aggressive/more precise model has a higher precision than recall. In some embodiments, the more aggressive model(s) have a recall of at least 0.85, 0.86, 0.87, 0.88, 0.89, 0.90, 0.91, 0.92, 0.93, 0.94, or 0.95. In some embodiments, the more aggressive model(s) have a precision of at least 0.84, 0.85, 0.86, 0.87, 0.88, 0.89, 0.90, 0.91, 0.92, 0.93, or 0.94. In some embodiments, the more precise model(s) have a recall of at least 0.84, 0.85, 0.86, 0.87, 0.88, 0.89, 0.90, 0.91, 0.92, 0.93, or 0.94. In some embodiments, the less aggressive model(s) have a precision of at least 0.85, 0.86, 0.87, 0.88, 0.89, 0.90, 0.91, 0.92, 0.93, 0.94, or 0.95.

In some embodiments, multiple ensemble machine learning techniques are used to generate a corresponding multiple types of predictions, which may be based on different types of medical data acquisition devices. For example, certain models and ensembles using those models may be directed to specific or unique combinations of sensor data (e.g., heart rate and temperature), while other models and ensembles using those other models may be directed to different combinations of sensor data (heart rate, blood pressure, EKG, blood sugar levels). In some cases, different models and/or ensembles are used for different types of predictions (hypoglycemia, seizure, stroke, blood loss, heart attack, etc.). Accordingly, the platforms, systems, devices, software, and methods disclosed herein can include an ensemble modelling technique that utilizes a plurality of ensemble machine learning models to generate a plurality of corresponding predictions using distinct types of health data.

As an illustrative example, the ensemble is created using two machine learning models: a CNN 612 and a tree-based model 616. The ensemble architecture may arrange the models parallel to each other, as they operate independently from each other in the real-time processing of the data. The models can be configured to have similar computation time for the input matrix and to compute faster than the frequency of the new input matrixes. Different models used in the ensemble modelling technique can be configured to have different levels of aggression in prediction of changes in patient health status. The predictions of these various models can then be integrated using a decision logic that is configured to balance the proactivity and accuracy of the alert.

In some embodiments, the ensemble comprises a CNN model 612 configured to be more aggressive to predict changes in patient status and a Tree-based model 616 configured to be more conservative and have lower false-positives in predicting changes. In some embodiments, static information is consumed differently based on the model type. For a CNN, the static information may be part of the matrix without requiring an explicit call out, as the model will automatically integrate this data into its overall training and prediction. For a Tree, the static information may be called out as categorical information and the pathways of the tree architecture is configured to account for these different categories. In some embodiments, the CNN is able to identify latent patterns of the static information on the prediction, as compared to a tree-based model that is more logical in its pattern creation.

In some embodiments, each model used in the ensemble modelling technique generates a prediction for each input dimensional matrix. In some embodiments, the ensemble modelling technique utilizes at least 2, 3, 4, 5, 6, 7, 8, 9, or 10 predictive models configured to generate predictions for one or more health statuses or conditions. In some embodiments, multiple models are configured to generate predictions regarding the same health status or condition. As an example, both the CNN model 612 and the Tree-based model 616 can make a prediction for each input predetermined dimensional matrix. The CNN model 612 may generate a CNN prediction label 614 and the Tree-based model 616 may generate a tree prediction label 618. As an illustrative example, the prediction label may either be a numerical value such as 0, a 1, or a 2, based on if the model predicts that the patient will be stable, low risk, high risk, respectively. The prediction for both models may be combined in a decision logic model 620 to generate a final alert prediction 630 while optimizing proactivity and false positive reduction using feature decomposition information 635. The final prediction 630 may be output to an alert generation module 640 to generate one or more alerts based on the prediction data, as described herein. There are many ways to design this combination strategy based on each model's performance metrics (proactivity, false positive levels).

For example, in one scenario, the CNN outputs a score of 1, but the Tree outputs a score of 0. Because the CNN is more aggressive, and the tree has not verified this prediction, the alert generation may wait for the next prediction. In the following prediction, if the CNN still outputs a 1 or if the tree outputs a 1, then an alert is output. By adding this decision tree-based check, the CNN prediction may be verified or its aggressive nature may be dampened. In the scenario, that both the CNN and Tree output a 1, then the alert generation may skip any delays or hysteresis and immediately send an alert, thereby increasing proactivity.

In some embodiments, the logic is adapted for higher risk alerts to integrate the predictions. In some embodiments, if the CNN predicts a 2 and Tree predicts a 0, then the alert generation will wait for the Tree to predict at least a 1 before it outputs the alert. As a high criticality alert must have low false-positives, the speed of the CNN may be utilized while not having to wait for the tree to have a high confidence before transmitting an alert. In the scenario that the Tree outputs a 2, but not the CNN, then an alert may be output since the tree has a lower false positive than the CNN.

In some embodiments, the architecture of the ensemble model allows for the expansion of the ensemble to include more parallel models that receive a matrix and make a prediction. These models may be optimized to look for other changes in patient status, for example, sepsis. The output of this model's prediction can be integrated into the overall alerting strategy. This allows the ensemble to continue to increase proactivity and reduce false positives for multiple patient health statuses.

In some embodiments, the health status prediction module (130) also removes and reduces false alarms from the one or more predictive alerts generated by utilizing a tree-based gradient boosting technique for a cross-verification process based on computation of a predictive value. Hysteresis may be implemented to reduce alarm fatigue. In some embodiments, notification or the one or more predictive alerts may be fired in a stepwise manner based on the clinical severity predicted for the patient. For example, '0' for no alarm, '1' and '2' for escalation across different alerting pathways.

In some embodiments, hysteresis delays generation of an alert if the input conditions which contribute to the alert do not last longer than a predetermined elapsed time period. In some embodiments, hysteresis is introduced to the system to increase the threshold value.

In some embodiments, the health status prediction module (130) implements an online training technique to fine-tune a prediction model corresponding to one or more clinical and operational requirements of an area of implementation or the patient health condition. The online training technique may enable the prediction model to fine-tune a prediction layer to specific clinical and operational requirements. As a result, the prediction-model may fine-tune itself to different clinical and operational requirements such as yielding better predictions for a departments or facilities specific patient population or fine-tuned for specific patient conditions.

Figure 2:
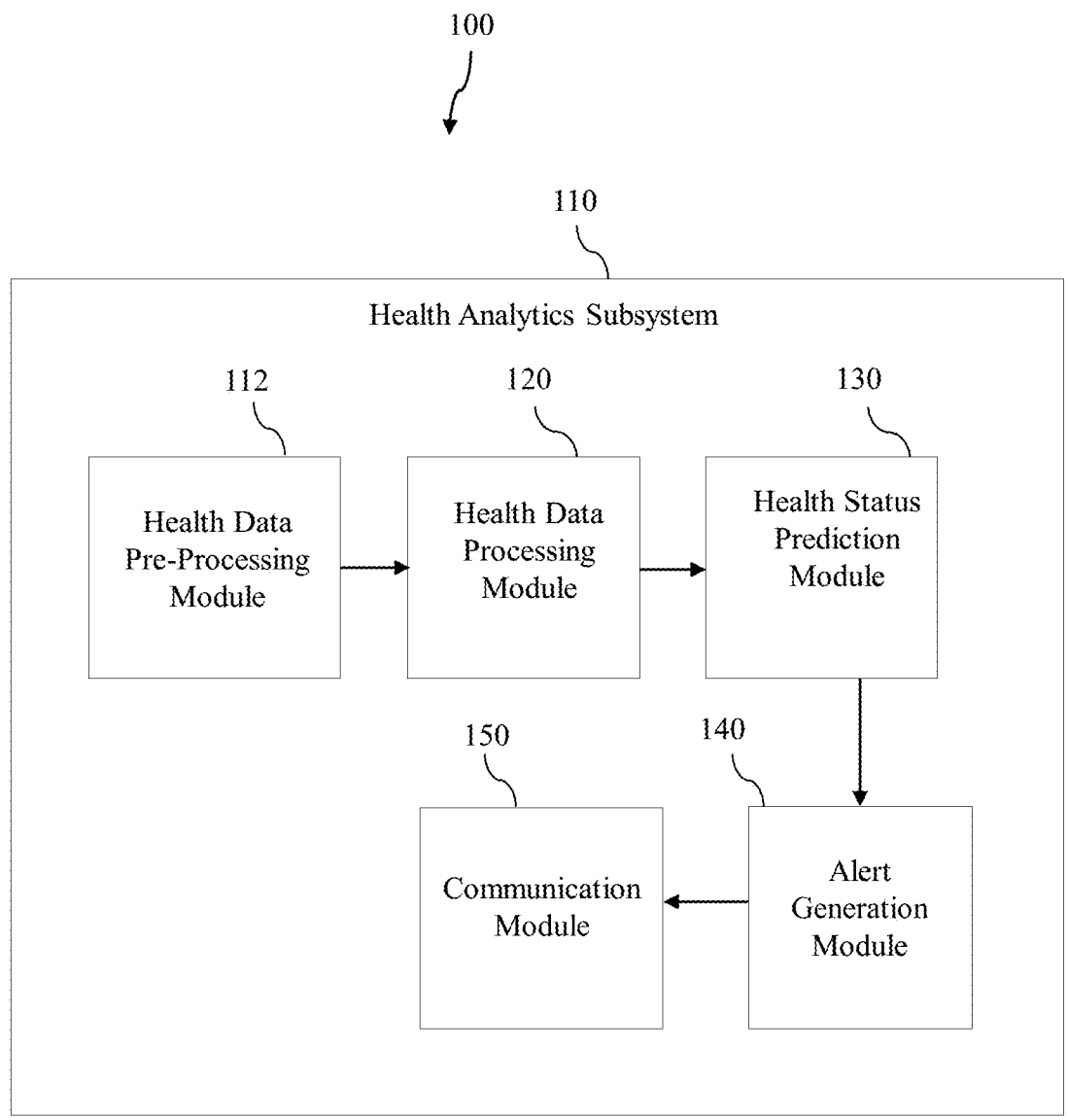
FIG. 2 is a block diagram representation of some embodiments of a health monitoring system for one or more patients of FIG. 1.

FIG. 2 is a block diagram representation of a health monitoring system (100) for one or more patients of FIG. 1 in accordance with some embodiments of the present disclosure. As described in aforementioned FIG. 1, the system (100) may include a health analytics subsystem (110), a health data pre-processing module (112), a health data processing module (120), and a health status prediction module (130). In some embodiments, the system (100) further includes an alert generation module (140) to generate one or more predictive alerts for the one or more patients based on prediction of the health status of the one or more patients. In some embodiments, the one or more predictive alerts generated are described with one or more contributing input features using an alert or feature decomposition technique. An illustrative example of an alert or feature decomposition technique is use of a class activation map. The class activation map technique determines the one or more input contributing features responsible for successful prediction of clinical scores in multiclass prediction in a feature decomposition process. In some embodiments, class activation map techniques are utilized to identify input features which are most likely to contribute to successful predictions. While class activation map is generally a technique used to identify discriminative regions in an image, this approach can be effective as used herein because a 2D matrix of health/sensor data is similar to an image, which is essentially a 2D matrix of pixels.

In some embodiments, the class activation map technique understands the one or more contributing input features and professional clinician verification for better prediction of the health status. The class activation map technique may utilize the information of the one or more contributing input features in the one or more predictive alerts sent to a clinical team for providing better descriptive information. For example, prediction of the health status of the one or more patients generated by the health status prediction module (130) may be a multi-class prediction by scoring into a zero cluster, a first cluster and a second cluster based on the level of predicted risk. In some embodiments, the class activation map technique makes the multiclass prediction more descriptive by depicting an exact input feature responsible for a corresponding cluster.

In some embodiments, the alert generation module (140) is configured to add hysteresis for providing one or more escalation processes based on a plurality of prediction classes predicted by the health status prediction module (130). In some embodiments, the alert generation module (140) transmits the one or more predictive alerts to one or more corresponding stakeholders for creating awareness associated with the health status of the one or more patients based on the predictive value. In some embodiments, the alert generation module (140) prioritizes a list of the one or more patients with a predictive value higher than a predetermined predictive value based on transmission of the one or more predictive alerts. As used herein, the term 'predictive value' is defined as a health status risk score associated with the one or more patients. Similarly, the term 'predetermined predictive value' is defined as a threshold value of the health status risk score associated with the one or more patients. The prioritization of the list may include the one or more patients with a high predictive value in comparison with the predetermined predictive value at a top position and the one or more patients with a low predictive value as compared to the predetermined predictive value are at a bottom position. In some embodiments, the system includes a clinician interface to display a prioritized list of patients. Accordingly, the provisioning of a prioritized list of patients allows a healthcare practitioner to triage and/or prioritize in order of predicted importance.

In some embodiments, the system (100) further includes a communication module (150) to send predicted health status of the one or more patients and the one or more predictive alerts to one or more computing devices associated with at least one of the one or more patients and/or one or more stakeholders associated with the one or more patients. In some embodiments, the one or more stakeholders may include at least one of one or more caregivers, nurses, healthcare practitioners, combinations thereof, and the like. In some embodiments, the one or more predictive alerts are channeled through the health analytics subsystem back to the handheld computing devices associated with the one or more stakeholders and also to the one or more medical data acquisition devices for bedside visualization of predictive risk. In some embodiments, visualization of predictive risk may be provided in a form of one or more colored icons on the display interface. The one or more predictive alerts may be sent to the handheld computing device for automatic prioritization of the one or more patients on the with highest predictive risk. In some embodiments, the alert generation module (140) further receives a feedback response corresponding to the one or more predictive alerts from the one or more stakeholders. The feedback response may include a helpful response, or an unhelpful response corresponding to the one or more stakeholders.

Figure 3:
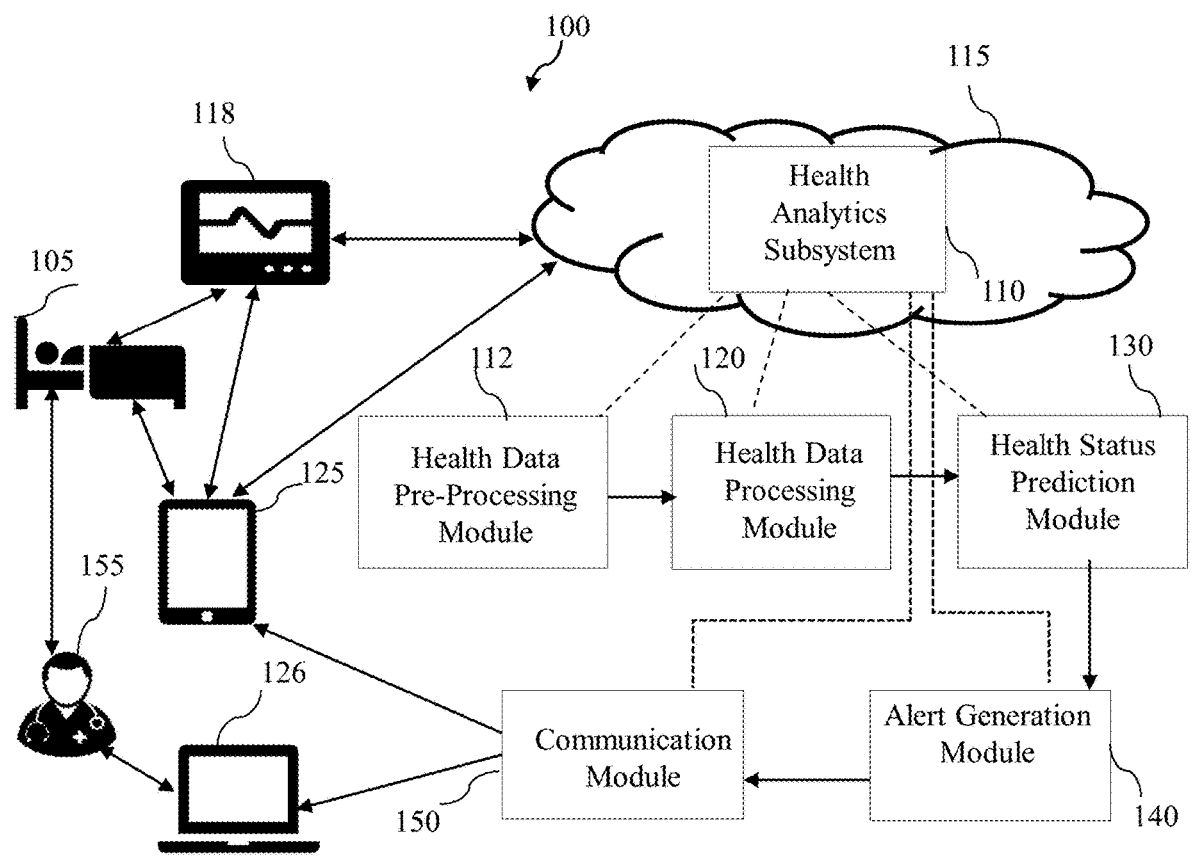
FIG. 3 illustrates a schematic representation of an exemplary system for a health monitoring system for one or more patients of FIG. 1 in accordance with some embodiments of the present disclosure.

FIG. 3 illustrates a schematic representation of an exemplary system for a health monitoring system (100) for one or more patients of FIG. 1 in accordance with some embodiments of the present disclosure. In some embodiments, the health monitoring system (100) aids in monitoring the health condition of one or more patients remotely and generating proactive alerts before onset of change in health status of the one or more patients. Considering an example, wherein a patient (105) from the one or more patients is suffering from a cardiac disorder. In such a scenario, remote monitoring of the patient (105) is essential as situation of the patient (105) is critical. As an example, in the scenario that a patient (105) is admitted in a hospital and ratio of healthcare practitioners to patients is insufficient, the system (100) disclosed herein can provide automated monitoring the health of the one or more patients by collecting health data of the one or more patients, analyzing such collected data (e.g., in a cloud based platform or locally), generating proactive alerts before the onset of change in the health status, thus enabling the healthcare practitioners to provide better health service.

In some embodiments, a health analytics subsystem (110), which is optionally hosted on the cloud-based platform (115), collects at least one of real-time patient demographic information, disease state information, one or more customizable health metrices, or a combination thereof. The health analytics subsystem (110) may include a health data pre-processing module (112) to receive health data representative of multiple health parameters of a patient (105) from a medical data acquisition device (118). In some embodiments, the medical data acquisition device includes a bedside monitoring device which collects the multiple health parameters such as at least one of a heart rate, a blood oxygen level, electrical signals produced by a heart, a respiratory rate, a blood pressure, a body temperature, or a combination thereof. In some embodiments, the medical data acquisition device includes at least one communication medium to receive the multiple health parameters from one or more sensors and a display interface. The display interface may display a real-time status of the health data collected from the patient (105).

In some embodiments, the system (100) includes a handheld computing device (125) associated with the patient (105) and a handheld electronic device (126) associated with one or more stakeholders (155). The handheld computing device (125) associated with the patient (105) can connect to the medical data acquisition device (118) to simultaneously collect data of the patient (105) and enable streaming of such collected data using a communication network. For example, the communication network may include a wireless communication network such as Bluetooth technology. Once, the health data is collected, pre-processing of the health data may be required. For pre-processing, the collected health data may be filtered through elimination of one or more outliers by the health data pre-processing module (112). For example, the one or more outliers may include at least one of additional movements of the one or more patients, misplacement of one or more sensors, one or more data artifacts, one or more noises or a combination thereof. In some embodiments, if an outlier data is detected, the data is removed from the matrix. In some embodiments, removed outlier data is replaced by up-sampled or down sampled data to fill in the matrix.

In some embodiments, outliers are identified by monitoring signal strength and setting thresholds on a per vital basis. In some embodiments monitored signal strengths include light signal strength, pressure wave strength, and electrical activity strength. In some embodiments, motion artifacts are identified and removed utilizing a bandpass frequency analysis for noise reduction. In some embodiments, a misplacement of sensors is determined by analyzing data obtained by said sensors. In some embodiments, the system detects a misorientation of one or more sensors via waveform analysis. In an example, if a pulse-oximeter is placed on the same arm as a blood pressure cuff, the system may determine that the data from a pulse oximeter is being distorted a blood pressure cuff inflates. The system may alert a clinician that the pulse oximeter should be relocated to the other arm of the patient.

In some embodiments, a health data processing module (120) creates a predetermined dimensional matrix representative of multiple samples (e.g., sensor data parameters or readings) obtained from a moving window of filtered health data in a predefined interval. In the example used herein, the predetermined dimensional matrix may include a two-dimensional matrix. Further, the predefined time interval may include duration of two hours. The moving window may move at any interval of the filtered health data flow. Since, the filtered health data may flow at different rates, the health data processing module (120) may enable either down-sampling technique or up-sampling technique to ensure the 2D matrix is sufficiently full. In some embodiments, a sample corresponds to a two-dimensional matrix which is input into the machine learning or artificial intelligence algorithm of the system. In some embodiments, sampling is continuous as new data is received. In some embodiments, the matrices are monitored to ensure that they are sufficiently full to make accurate predictions.

Again, selection of one or more samples from the multiple samples of the predetermined dimensional matrix are enabled by the health data processing module (120) based on a predefined condition. For example, the predefined condition may include selection of the one or more samples which have more than 3 health parameters for 80% of the predefined duration are selected. Each sample from the one or more patients, is treated independently for training of the model as one patient may have multiple samples. When no values are available or a not a number (NaN) values are obtained, such spaces are replaced by (−1 or 0) for a convolutional neural network (CNN) to ensure the data is not considered. A tree-based technique handles non-zero values. The health data processing module (120) also processes static information associated with the one or more patients as fixed data across the predetermined dimensional matrix in real-time, wherein the static information may include but not be limited to, patient demographics, patient health condition, one or more clinical notes and the like.

In some embodiments, the health data processing module (120) implements one or more confidence improving strategies such as hysteresis, low pass filtering, and rules determined from clinical knowledge of the scores, to lead to a true positive based on at least one of human physiology or a combination thereof. The health data processing module (120) may also normalize the predetermined dimensional matrix of health parameters in a common range with respect to entire data available and thereby remove eliminate local maximums and local minimums.

In some embodiments, after the filtered health data is processed by preparation of the predetermined dimensional matrix, the predetermined dimensional matrix is utilized for analysis and prediction of the health status of the one or more patients (105). For example, the predetermined dimensional matrix with unlabeled data may be labelled using a clustering technique, wherein the clustering technique utilizes results from one or more clinical deterioration techniques. In one example, the one or more clinical deterioration scoring techniques may include at least one of a modified early warning scoring technique, universal vital assessment technique, a quick sequential organ failure assessment technique (qSOFA), or a combination thereof.

In some embodiments, after the labelling is completed, prediction of an onset of change in the health status of the patient is performed in real-time using an ensemble modelling technique by a health status prediction module (130). In some embodiments, herein the ensemble modelling technique includes at least one of a dilated causal convolution network, a tree-based gradient boosted technique, a recurrent neural network, a graph neural network, a support vector machine classifier, a logistic regression technique, a k-nearest neighbor classifier, or a combination thereof. In some embodiments, if the sensor or vital sign data of the patient (105) suddenly starts fluctuating within a predefined threshold limit, the health status prediction module (130) analyses the fluctuations and increase the predicted risk score and send an alert before onset of cardiac arrest. As an illustrative example, when the heart rate or pulse rate of the patient, which is collected from the one or more sensors, suddenly begins fluctuating within the predefined threshold limit, the health status prediction module then analyses the fluctuations and increases the predicted risk score and optionally sends an alert before onset of cardiac arrest.

In some embodiments, the predictive model(s) disclosed herein (e.g., as part of an ensemble modelling technique) comprise a neural network such as a convolution neural network (CNN). In some embodiments, the CNN is a 1-D CNN. In some embodiments, the predictive model comprises a 1-D CNN boosted with a tree-based algorithm for generating a predictive alert. A convolution neural network (CNN) can comprise distinct layers to transform the received input into an output. The input may be the one or more health parameters and the output may be one or more predictive alerts or predictive values used as part of the ensemble model process. In some embodiments, the CNN comprises one or more convolution layers. The convolution layers may comprise a set of learnable filters. In some embodiments, the convolution layers compute the dot product between the entries of the filter and the input and producing a 2-dimensional activation map of that filter. As a result, the network may learn filters that activate when it detects some specific type of feature at some spatial position in the input. In some embodiments, the ensemble model comprises a CNN and tree sub-models. The sub-models may consolidate the data inputs from multiple sensors to produce a single output in a predictive layer.

In some embodiments, the CNN may comprise one or more pooling layers. Pooling may be implemented by a non-liner function to partition the input matrix into a set of non-overlapping rectangles. In some embodiments, the pooling layer outputs the maximum value of each portioned sub-region. The pooling layer may progressively reduce the spatial size of the matrix to reduce memory footprint and increase computation speed. Pooling layers may be inserted between convolution layers of the CNN.

Further, after prediction, an alert generation module (140) may generate one or more predictive alerts for the patient (105). For example, the one or more predictive alerts which are generated may be further made more descriptive to depict the one or more contributing input features with help of implementation of a class activation map technique, wherein the class activation map technique determines one or more input features responsible for successful prediction of clinical scores. The class activation map technique may utilize the one or more important features and professional clinician verification for better prediction of the health deterioration. For example, the class activation map technique may determine a risk score of 2 is predicted due to fast respiratory rate.

In some embodiments, the systems and methods disclosed herein generate predictions or predictive values in association with health monitoring. The predictions or predictive values can be assessed for accuracy according to various metrics. The accuracy can be based on a testing data set of at least 100, 150, 200, 250, 300, 350, 400, 450, or 500 samples. In some instances, the predictions or predictive values are calculated at or above a statistical threshold. The accuracy, specificity, sensitivity, positive predictive value, negative predictive value, AUC, or any combination thereof may be determined for a prediction, for example, by testing the predictive model against a set of independent samples. True positive is a positive test result that detects the condition when the condition is present (e.g., detection of health condition or status deterioration). True negative is a negative test result that does not detect the condition when the condition is absent. False positive is a test result that detects the condition when the condition is absent. False negative is a test result that does not detect the condition when the condition is present. Accuracy is defined as the sum of true positive and true negative divided by the sum of true positive, true negative, false positive, and false negative. Specificity is defined as true negative divided by the sum of true negative and false positive. Sensitivity is defined as true positive divided by the sum of true positive and false negative. Positive predictive value is defined as true positive divided by true positive and false positive. Negative predictive value is defined as true negative divided by the sum of true negative and false negative. AUC refers to the area under the curve of a receiver operating characteristics curve (ROC), also referred to as AUROC (area under the receiver operating characteristics).

In some instances, the predictive model(s) disclosed herein provide an accuracy of at least 50%, 60%, 70%, 80%, 90%, 95%, 99% or more for at least 100, 200, 300, 400, or 500 or more independent samples. In some instances, the predictive model(s) disclosed herein provide a sensitivity of at least 50%, 60%, 70%, 80%, 90%, 95%, 99% or more for at least 100, 200, 300, 400, or 500 or more independent samples. In some instances, the predictive model(s) disclosed herein provide a specificity of at least 50%, 60%, 70%, 80%, 90%, 95%, 99% or more for at least 100, 200, 300, 400, or 500 or more independent samples. In some instances, the predictive model(s) disclosed herein provide a positive predictive value of at least 50%, 60%, 70%, 80%, 90%, 95%, 99% or more for at least 100, 200, 300, 400, or 500 or more independent samples. In some instances, the predictive model(s) disclosed herein provide a negative predictive value of at least 50%, 60%, 70%, 80%, 90%, 95%, 99% or more for at least 100, 200, 300, 400, or 500 or more independent samples. In some instances, the predictive model(s) disclosed herein provide an AUC of at least 0.5, 0.6, 0.7, 0.8, 0.85, 0.90, 0.95, or more for at least 100, 200, 300, 400, or 500 or more independent samples.

In some embodiments, the alert generation module (140) adds hysteresis to reduce alarm fatigue for providing one or more escalation processes based on a plurality of prediction classes predicted by the health status prediction module (130). Notification or the one or more predictive alerts may be generated in a stepwise manner based on the clinical severity predicted for the patient (105). For example, the alert generation module (140) may configure limits of the one or more alarms in such a manner that the limits between subsequent alarms should not be too wide or too low.

In some embodiments, the alert generation module (140) transmits the one or more predictive alerts to one or more corresponding stakeholders such as either doctors, nurses, patient party and the like, for creating awareness associated with a predicted health status change, for example, health deterioration of the patient (105) based on the predictive values. Additionally, the alert generation module (140) may also prioritize a list of the one or more patients with a predictive value higher than a predetermined predictive value based on transmission of the one or more predictive alerts. For example, if the patient (105) based on the predictive value is at higher risk, then the patient (105) may be placed at a top position in the priority list among one or more other patients. In examples used herein, the one or more predictive alerts may be received by the one or more stakeholders using one or more computing devices associated with the one or more stakeholders (155) via a communication module (150). The one or more predictive alerts may be sent from a cloud-based platform to the one or more stakeholders (155) and also to the medical data acquisition device for visualization of predictive risk in a form of a colored icon on the display interface.

Furthermore, the alert generation module (140) upon sending the one or more predictive alerts may also receive a feedback response corresponding to the one or more predictive alerts, from the one or more stakeholders. For example, the feedback response may include a helpful response, or an unhelpful response corresponding to the one or more stakeholders. The feedback response received from the one or more stakeholders may help in improving the prediction of the health status. In some embodiments, the system (100) serves an overall purpose by monitoring the health condition of the patient (105) by collecting the health data in the real-time, analyzing and prediction of a health status using an artificial intelligence technique and further generates the one or more predictive alerts before the onset of change in the health status for creating awareness.

In some embodiments, feedback from a stakeholder is used to train the artificial intelligence or machine-learning algorithm. For example, one or more ML predictive models used to detect health status changes can be further trained or re-trained using updated data sets incorporating feedback (e.g., new labelled data). The model can continue to fine-tune its predictive performance through batch wise retraining on smaller datasets incorporating the end use cases patient data and the feedback from the end users regarding performance. This allows the generic base model to achieve higher performance which considers the types of patient profiles commonly encountered in the area of implementation and the predictive requirements of the end user.

In some embodiments, feedback is generated by a response submitted by an end user or stakeholder. The response may comprise a binary response. For example, a user or stakeholder may be asked if an alert or notification is considered to be helpful or not helpful. Feedback may also include input as to if a notification or alert was issued timely or not. In some embodiments, the feedback is added to the 2D matrix as a label. The feedback may be utilized in training of the system. In some embodiments, the feedback is utilized in an online training of the system. In some embodiments, the feedback is included in a retraining set utilized to continuously optimize or customize the system.

In some embodiments, the ensemble model or one or more predictive models used by the ensemble modelling technique is fine-tuned for users, for example, specific departments, hospitals, or other parties, by using an online training strategy. When alerts are sent out to the clinical teams, they can receive feedback on whether they are helpful or not. In some embodiments, user feedback is added to the pre-determined matrix as one or more additional columns. A matrix with the feedback can be stored as a new training dataset. Creating a new training dataset with this feedback can be important since the predictions can lead to clinical interventions, which means the data created for when the system utilized on patients may be potentially impacted by clinical intervention. Accordingly, in some embodiments, the one or more predictive models of the ensemble modelling technique are re-trained or updated based on the new training dataset. For example, the feedback may include an indication that a predicted health status deterioration was incorrect, thereby causing a matrix that gave rise to the prediction to be re-labelled. Such relabeled matrixes can be used to better train one or more predictive models.

In some embodiments, an online training session is triggered whenever a sufficient or threshold amount of new responses are received, for example, every 100 feedback responses. In some embodiments, an online training session comprises re-training one or more predictive models using these new matrixes as input data-sets. This retraining impacts the machine learning models that are a part of the ensemble. For example, the CNN and tree-based method parameters may be adjusted to account for the feedback received from clinicians. This may allow the model to continue learning and adapting to new patient conditions. In some embodiments, online training sessions are triggered periodically or according to an update schedule.

Figure 4:
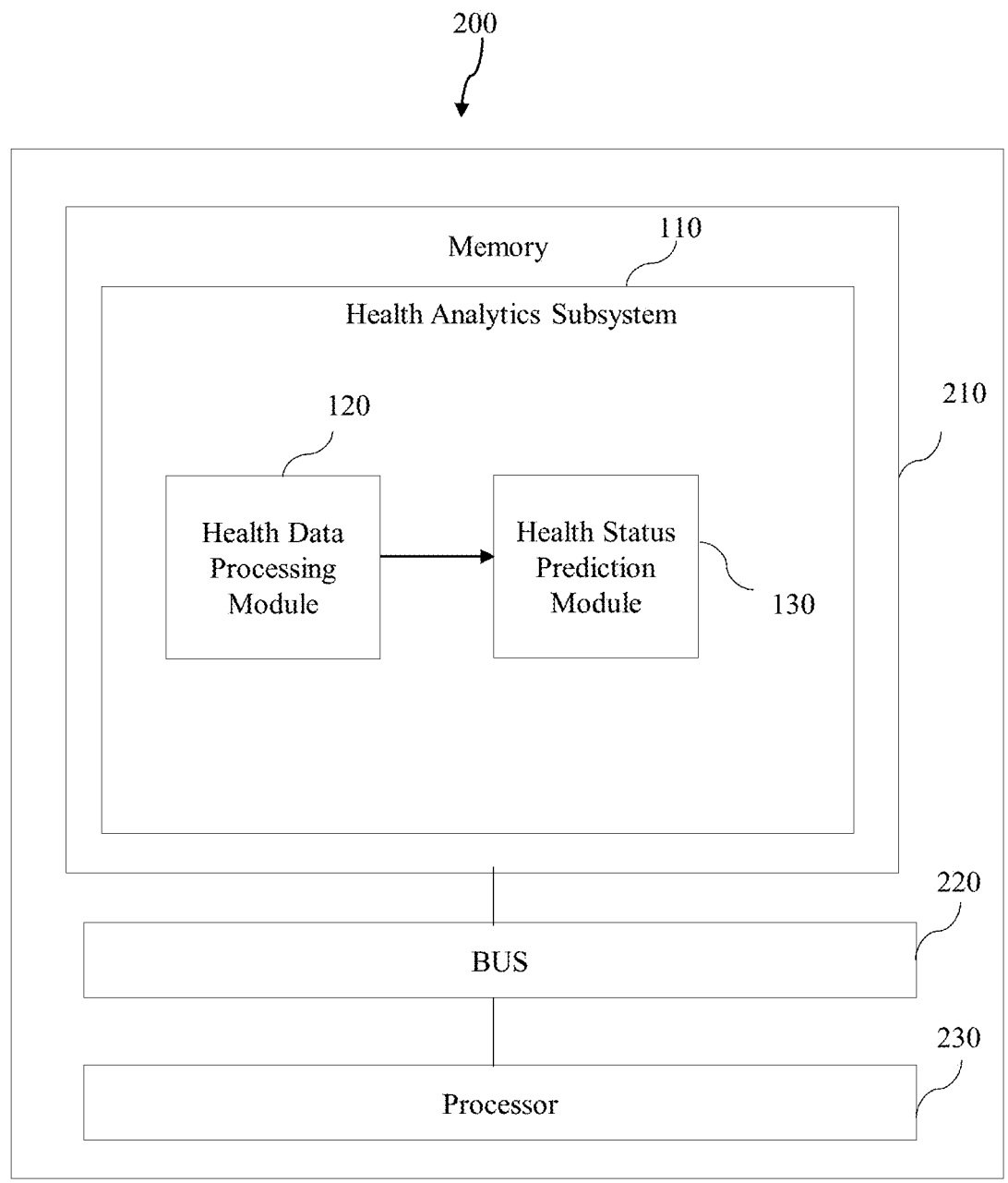
FIG. 4 illustrates a block diagram of a computer or a server in accordance with some embodiments of the present disclosure.

FIG. 4 illustrates a block diagram of a computer or a server in accordance with some embodiments of the present disclosure. The server (200) may include processor(s) (230), and memory (210) operatively coupled to the bus (220). The processor(s) (230), as used herein, may refer to any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a digital signal processor, any other type of processing circuit, or a combination thereof.

The memory (210) may include several subsystems stored in the form of an executable program which instructs the processor (230) to perform the method steps illustrated in FIG. 1. The memory (210) may be substantially similar to a system (100) of FIG. 1. The memory (210) may have the following subsystems: a health analytics subsystem (110), a health data pre-processing module (120), a health data processing module (120) and a health status prediction module (130).

The health analytics subsystem (110) may include a health data processing module (120) to create a predetermined dimensional matrix representative of a multiple of samples obtained from a moving window of filtered health data representative of a plurality of health parameters of the one or more patients in a predefined interval. The health data processing module (120) may process one or more samples selected from the multiple of samples of the predetermined dimensional matrix based on a predefined condition. The health analytics subsystem (110) may also include a health status prediction module (130). In some cases, the health status prediction module is referred to as a future event prediction module. For example, a health status prediction can include a current health status or condition, whereas a future event prediction can be directed to future events that are predicted to occur based on current real-time health data such as a change in health status after the time period of the health data (e.g., timestamps of medical sensor data monitoring the patient). In some cases, the future event is not a detection of a current or ongoing health status, but rather a health status or change in health status that takes place during a time in the future. For example, a future event may be detected or predicted to take place in the near future within a maximum time period or threshold, or alternatively or in combination, at least a minimum time period or threshold following the current window of health data used to generate the prediction. This time period of window of detection can be adjusted for specific types of events or predictions. In some cases, the future event is detected at a minimum of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 in the future after the current window of health data. Alternatively or in combination, the future event is detected within the next 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes after the current window of health data. In some cases, the future event is detected at a minimum of at least 1, 2, 3, 4, 5, 6, 7, 8, 9, 10, 11, 12, 13, 14, 15, 16, 17, 18, 19, 20, 21, 22, 23, or 24 hours in the future after the current window of health data. Alternatively or in combination, the future event is detected within the next 1, 2, 3, 4, 5, 6, 7, 8, 9, 10, 11, 12, 13, 14, 15, 16, 17, 18, 19, 20, 21, 22, 23, or 24 hours after the current window of health data.

The health status prediction module (130) labels the predetermined dimensional matrix upon processing of the one or more samples using one or more clinical deterioration scoring techniques. The health status prediction module (130) may also predict onset of change in the health status of the one or more patients in real-time using an ensemble modelling technique upon labelling of the predetermined dimensional matrix.

The bus (220), as used herein, may refer to be internal memory channels or computer network that is used to connect computer components and transfer data between them. The bus (220) may include a serial bus or a parallel bus, wherein the serial bus transmits data in bit-serial format and the parallel bus transmits data across multiple wires. The bus (220) as used herein, may include, but is not limited to, a system bus, an internal bus, an external bus, an expansion bus, a frontside bus, a backside bus and the like.

Figure 5:
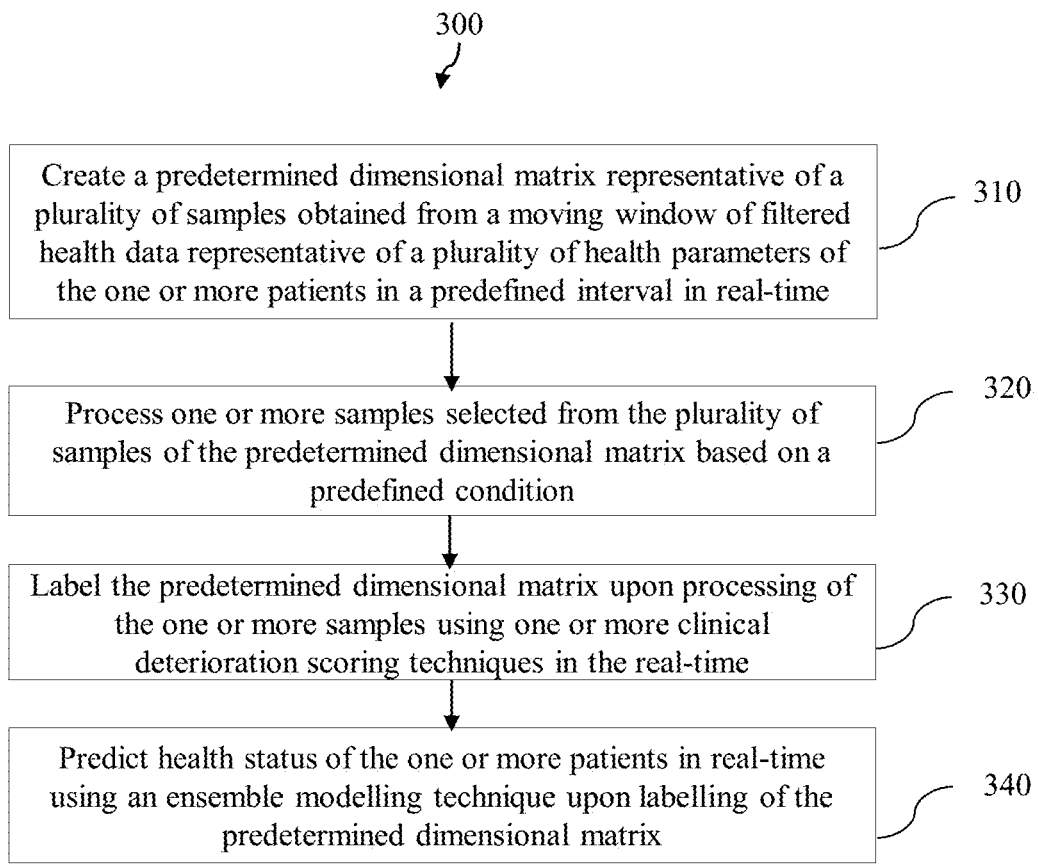
FIG. 5 is a flow chart representing the steps involved in a method to operate a health monitoring system for one or more patients of FIG. 1 in accordance with some embodiments of the present disclosure.

FIG. 5 is a flow chart representing the steps involved in a method (300) to operate a health monitoring system for one or more patients of FIG. 1 in accordance with some embodiments of the present disclosure.

In some embodiments, the systems and methods (300) disclosed herein include creating a predetermined dimensional matrix representative of a multiple of samples obtained from a moving window of filtered health data representative of a plurality of health parameters of the one or more patients in a predefined interval in step 310. In some embodiments, creating the predetermined dimensional matrix representative of the multiple of samples includes creating a two-dimensional matrix of the multiple samples obtained from the moving window of filtered health data within two-hour duration. In some embodiments, the predetermined dimensional matrix is down sampled or up sampled to ensure the predetermined dimensional matrix is sufficiently full. In some embodiments, creating the predetermined dimensional matrix includes creating predetermined dimensional matrix by receiving the health data representative of the multiple of health parameters of the one or more patients such as at least one of a heart rate, a blood oxygen level, electrical signals produced by a heart, a respiratory rate, a blood pressure, a body temperature, or a combination thereof. In some embodiments, receiving the health data representative of the multiple of health parameters of the one or more patients from the one or more medical data acquisition devices includes receiving the health data from a bedside monitoring device which includes at least one communication medium to receive the multiple health parameters from one or more sensors and a display interface.

The systems and methods (300) may also include processing one or more samples selected from the multiple of samples of the predetermined dimensional matrix based on a predefined condition in step 320. In some embodiments, processing the one or more samples selected from the multiple samples of the predetermined dimensional matrix based on the predefined condition includes processing the one or more samples selected from the multiple samples based on selection of the one or more samples which have more than 3 health parameters for 80% of the predefined duration.

The systems and methods (300) may also include labelling the predetermined dimensional matrix upon processing of the one or more samples using one or more clinical deterioration scoring techniques in step 330. In some embodiments, labelling the predetermined dimensional matrix upon processing of the one or more samples using the clinical deterioration technique includes labelling the predetermined dimensional matrix using at least one of a modified early warning scoring technique, universal vital assessment technique, a quick sequential organ failure assessment technique (qSOFA) or a combination thereof.

The systems and methods (300) may also include predicting, by the health status prediction module, onset of change in the health status of the one or more patients in real-time using an ensemble modelling technique upon labelling of the predetermined dimensional matrix in step 340. In some embodiments, predicting the health status of the one or more patients using the ensemble modelling technique includes predicting the health status using at least one of a dilated causal convolution network, a tree-based gradient boosted technique, a recurrent neural network, a graph neural network, a support vector machine classifier, a logistic regression technique, a k-nearest neighbor classifier or a combination thereof. In such embodiment, the dilated causal convolution networks may be utilized for aggressive and fast prediction of the health status of the one or more patients. In some embodiments, the tree-based gradient boosted technique is utilized for reducing one or more false positives. In some embodiments, the ensemble modelling technique balances the prediction of the health status and also removes false alarms.

In some embodiments, the systems and methods (300) further include generating one or more predictive alerts for the one or more patients based on prediction of the health status of the one or more patients. In some embodiments, the one or more predictive generated are described with one or more contributing input features by implementation of a class activation map technique. In some embodiments, the class activation map technique determines the one or more contributing input features responsible for successful prediction of clinical scores in multiclass prediction. In some embodiments, the class activation map technique utilizes the one or more important features and professional clinician verification for better prediction of the health status of the one or more patients.

In some embodiments, the systems and methods (300) further include transmitting the one or more predictive alerts to one or more corresponding stakeholders for creating awareness associated with the health status of the one or more patients based on the predictive value. In some embodiments, transmitting the one or more predictive alerts to the one or more stakeholders may include transmitting the one or more predictive alerts upon reducing and removing the one or more false alarms. In some embodiments, the method further includes prioritizing a list of the one or more patients with a predictive value higher than a predetermined predictive value based on transmission of the one or more predictive alerts.

In some embodiments, the systems and methods further include providing a web portal and/or mobile application for clinicians and stakeholders (and also patients themselves) to view and visualize the predictive alert and/or the health data that was used to generate the prediction leading to the alert. A web portal and/or mobile application can be made accessible to specific users, optionally with differential access to different types of information for different users. For example, certain access rules may prohibit third party access to confidential medical data in accordance with HIPPAA regulations. In some embodiments, the web portal and/or mobile application provides access to and/or displays historical data, real-time data, waveforms (e.g., for sensor data), historical and/or current alerts, information on users who have access to information via the portal/application and the types of information they are authorized to access, and other relevant information. In some embodiments, the web portal and/or mobile application allows users to communicate with each other, for example, sending messages (e.g., optionally including multimedia such as audio/video) and requesting an appointment or status check. In some embodiments, the application/portal allow for prioritization of patients based on the predicted risk, for example, arranging patients in order of severity or danger of the risk for a clinician portal displaying a list of current patients.

In some embodiments, the method further includes sending a predicted onset of change in the health status of the one or more patients and the one or more predictive alerts to one or more computing devices associated with at least one of the one or more patients and one or more stakeholders associated with the one or more patients. In some embodiments, the one or more stakeholders may include at least one of one or more caregivers, a nurse, a healthcare practitioner or a combination thereof. In some embodiments, the one or more predictive alerts are channeled through the health analytics subsystem back to the handheld computing devices associated with the one or more stakeholders and also to the one or more medical data acquisition devices for bedside visualization of predictive risk in a form of colored icon on the display interface. In some embodiments, the method further includes receiving a feedback response corresponding to the one or more predictive alerts from the one or more stakeholders. In some embodiments, the feedback response includes a helpful response, or an unhelpful response corresponding to the one or more stakeholders.

Figure 7A:
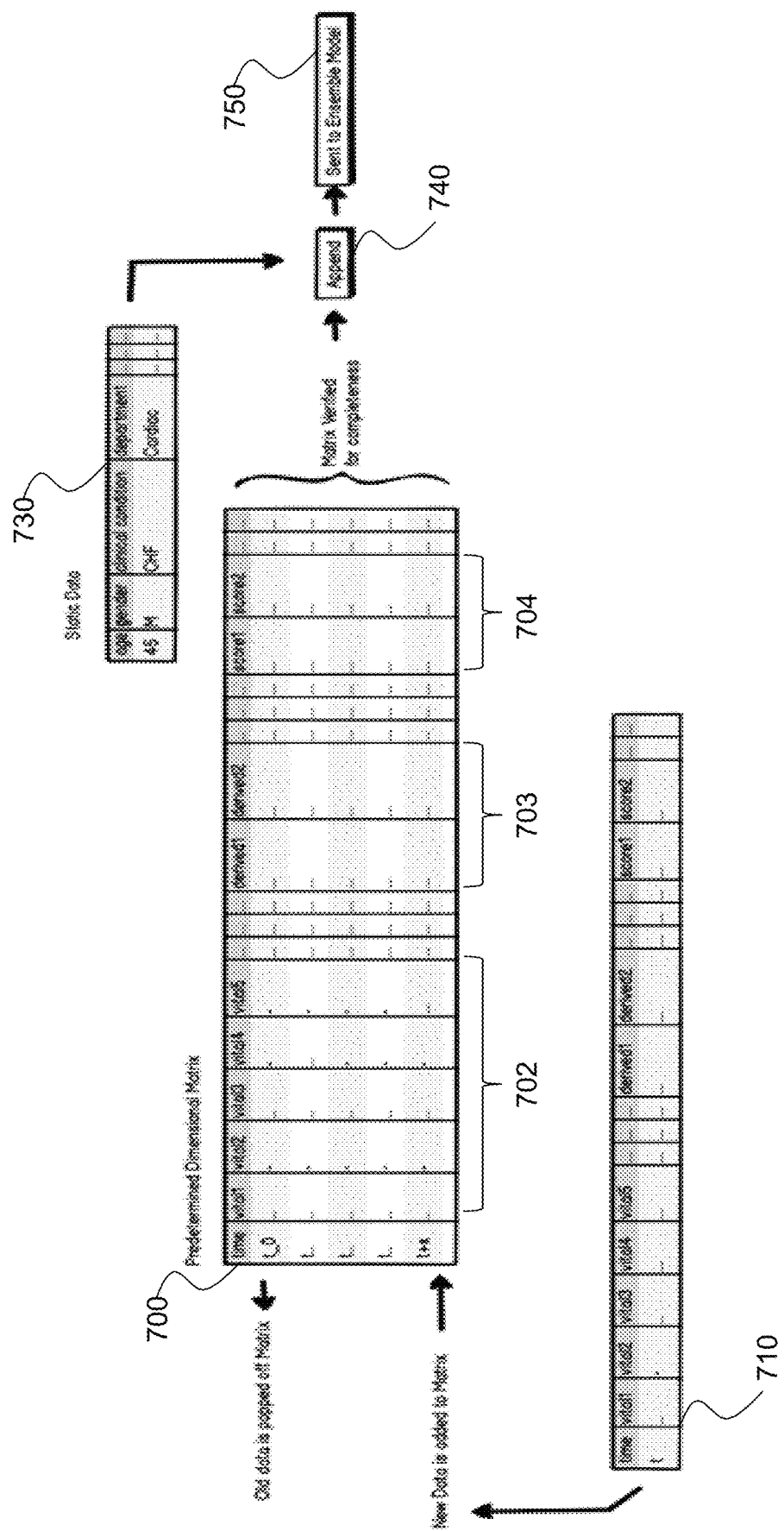
FIG. 7A and FIG. 7B depict a flow chart representing the steps involved in building a predetermined matrix of a health monitoring system in accordance with some embodiments of the present disclosure.
Figure 7B:
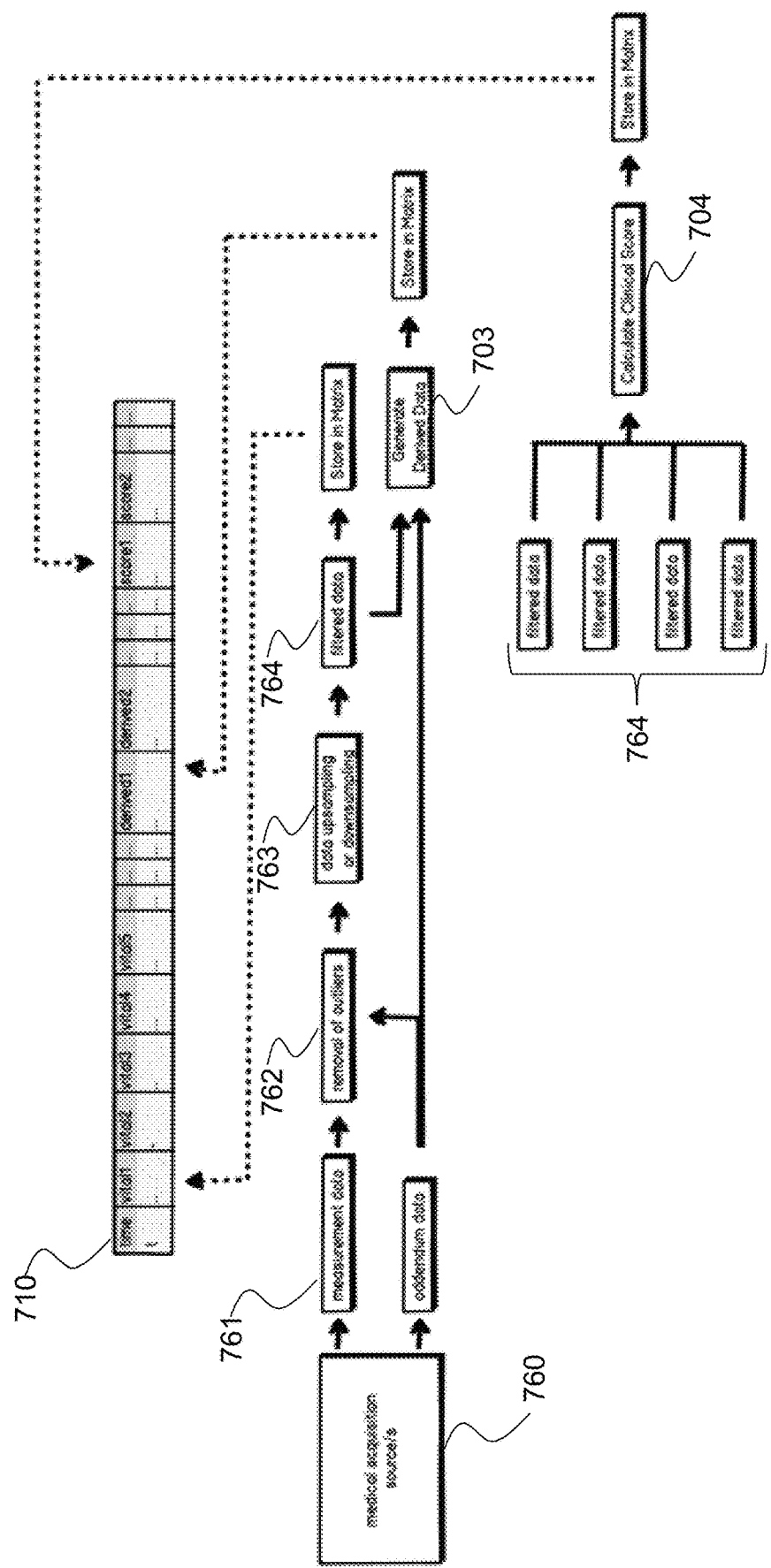

FIG. 7A and FIG. 7B depict embodiments of a predetermined dimensional matrix. In some embodiments, a 2D matrix 700 comprises a matrix of filtered measured health parameters 702, derived parameters 703, and calculated clinical scores 704. This matrix, once prepared, may be sent to the prediction module. In some embodiments, the matrix is built in real-time as new data 710 enters the system's pre-processing and processing modules. The 2D matrix may be considered a "predetermined matrix" because it may comprise a fixed predetermined size, or time window, and has a predetermined frequency for data to be entered. As an illustrative example, this can be a 2 hour window storing data at 3.33 millihertz (i.e. 1 data point per 5 minutes).

In some embodiments, multiple data streams are provided by multiple data acquisition devices 760. In some embodiments, three devices are provided. The input devices may comprise a pulse oximeter, a blood pressure cuff, and an electrocardiogram. Each of these data streams 761 may be provided at different frequencies and have different processing requirements to be entered into the 2D matrix. In addition, raw data may be filtered at step 762 to remove data artifacts.

In some embodiments, sampling at step 763 corresponds to the vital signal being sampled. If a frequency of the vital signal being sampled is higher than the frequency selected for the 2D matrix, the data may be down-sampled to fit the 2D matrix frequency. For example, if the pulse oximeter obtains data at a frequency of 30 Hz, the data may be down-sampled to the 3.33 millihertz frequency of the matrix. Data may also be up-sampled to fit the 2D matrix. For example, if the blood pressure cuff obtains data at a frequency of 0.2 millihertz, the data may be up-sampled to the 3.33 millihertz frequency of the matrix. In some embodiments, sampling will be utilized to fill gaps in the matrix created by the data filtering.

In some embodiments, the 2D matrix is filled with the final filtered data 764 that has been sampled to the same frequency requirements of the matrix. The 2D matrix may also be expanded with derived data. For example, an electrocardiogram is a picture of the electrical activity of the heart. Specific values from the electrocardiogram image may be extracted be input into the matrix. For example, a standard 3 lead electrocardiogram gives a heart rhythm picture that can create the following derived vital signs: PQ interval, QRS complex width, QT interval, arrythmia state, HR variability, etc.

The 2D matrix may then be expanded with the calculated risk score data. Multiple filtered vital signs may be utilized to then create new data to be added to the 2D matrix. For example, by using the modified early warning score system, with the information available for each row of the 2D matrix, a score can be calculated. For example, a patient with pulse rate of 76, a respiratory rate of 24, and blood pressure of 135/76, may be assigned an early warning score of 1.

In some embodiments, after matrix is now prepared, additional tests are performed at and appending module 740 prior to the matrix being sent to the model. These tests may ensure that the matrix can yield a high-quality prediction. In some embodiments, the test to be sent for consumption may at least 3 vital signs that have 80% of the matrix duration. If passed, then the model will have enough information to make a prediction The 2D matrix may be appended with static information 730 about the sample: demographics, disease state, etc. Then the matrix may be to the predictive model 750 for consumption.

Figure 9:
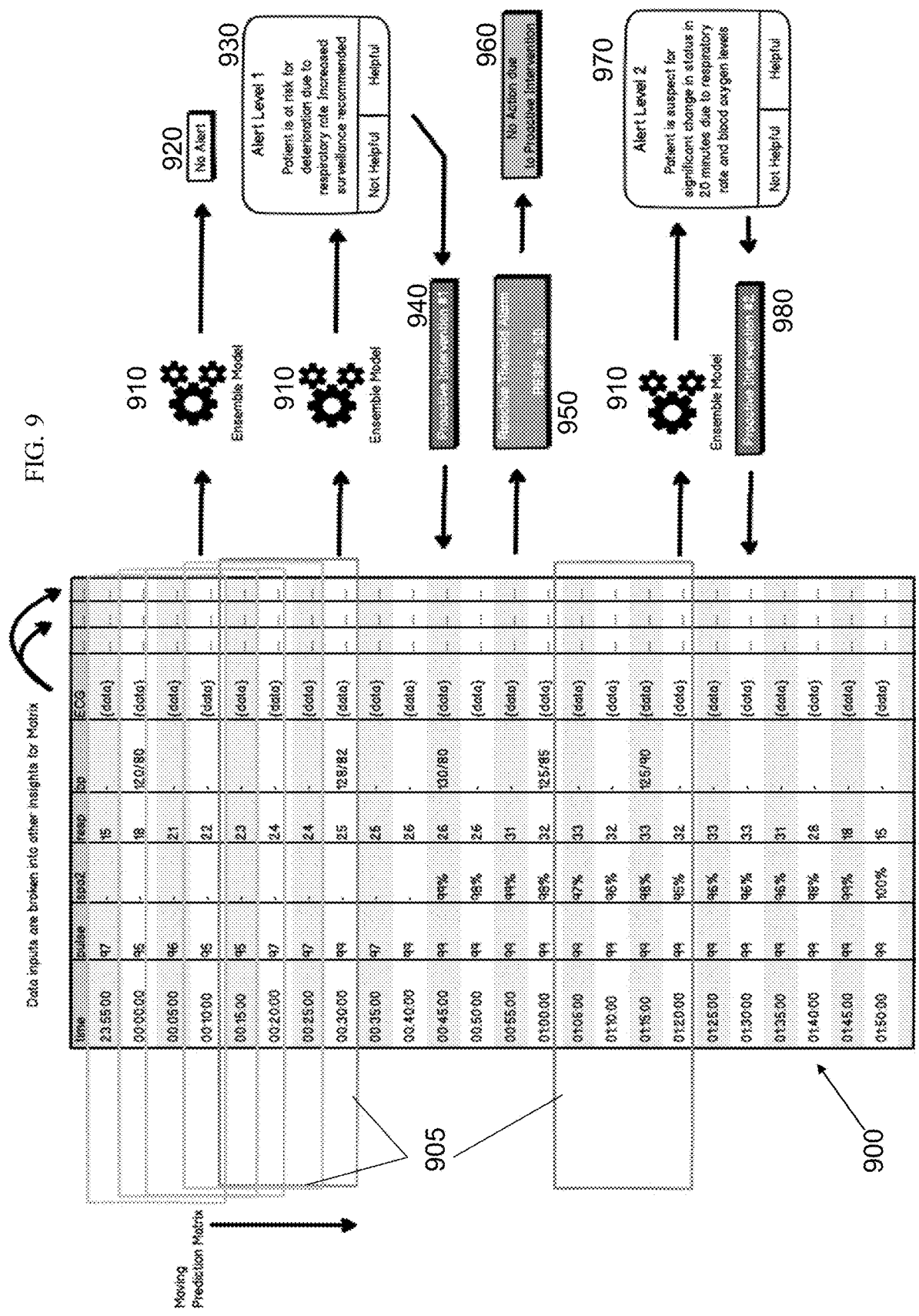
FIG. 9 depicts a computer system for implementing the methods of a health monitoring system in accordance with some embodiments of the present disclosure.

FIG. 9 depicts an embodiment of processing a 2D matrix. In some embodiments, a 2D matrix 900 comprises a matrix of filtered measured health parameters which are continually acquired from one or more sensors. In some embodiments, segments 905 of matrix are captured over a predetermined time period and sent to an ensemble model 910, as described herein. In some embodiments, as depicted in FIG. 9, a matrix segment 905 comprises 4 rows of data captured over 20 minutes.

In some embodiments, multiple data streams are provided by multiple data acquisition devices. In some embodiments, three devices are provided. The input devices may comprise a pulse oximeter, a blood pressure cuff, and ab electrocardiogram. Each of these data streams may be provided at different frequencies and have different processing requirements to be entered into the 2D matrix. In addition, raw data may be filtered at to remove data artifacts.

In some embodiments, the ensemble model determines a calculates a risk score of zero and no alert is generated at 920. In some embodiments, after no alert is generated, the model continues to evaluate the data using the predetermined thresholds. In some embodiments, no alert is generated when the average value of the measured health parameters of a matrix segment do not exceed reactive alarm threshold.

In some embodiments, the ensemble model analyzes a matrix segment and calculates a risk score of 1. A risk score of 1 may be calculated when one or more of the measured heath parameters exceeds a reactive alarm threshold when averaged over the duration of the matrix segment 905. The system may generate a level 1 alert 930, as described herein. The generated alert may accept feedback from a stakeholder, as described herein. Based on the feedback, a first proactive intervention 940 may be applied to the system. The first proactive intervention 940 may comprise an increase in a reactive alarm threshold.

In an example, as depicted in FIG. 9, an increase in the average respiratory rate of the matrix segments 905 may cause a generation of a level 1 alert 930. The feedback from received in response the level one alert may cause a first proactive intervention 940, which may raise the reactive threshold alarm 950 for the respiratory rate to an average of 30 breaths per minute, as exemplified in FIG. 9. Therefore, unless the average respiratory rate of a matrix segment reaches 30 breaths or more, an alert may not be generated. In some embodiments, one or more stake holders view information that no action is necessary due to the first proactive intervention at 960.

In some embodiments, if an average value of a measured health parameter exceeds the new reactive threshold, the ensemble model 910 generates a level 2 alert 970, as described herein. The generated alert level 2 may accept feedback from a stakeholder, as described herein. Based on the feedback, a second proactive intervention 970 may be applied to the system. The second proactive intervention 970 may change a reactive alarm threshold.

Various embodiments of the present disclosure may provide systems for health monitoring of the one or more patients from a remote environment by collection of health data without using any wearable device or implantation of body sensors in order to reduce discomfort or dependency of the one or more patients.

Moreover, the present disclosed systems may predict the onset of change in the health status of the one or more patients using the ensemble model which helps in accurate and aggressive prediction using the dilated causal convolution networks.

Furthermore, the present disclosed systems may also reduce and remove false alarms by removing the false positives using the tree-based technique which further reduces ambiguity among the one or more stakeholders associated with the one or more patients for managing healthcare of the one or more patients.

Computer Systems

Figure 8:
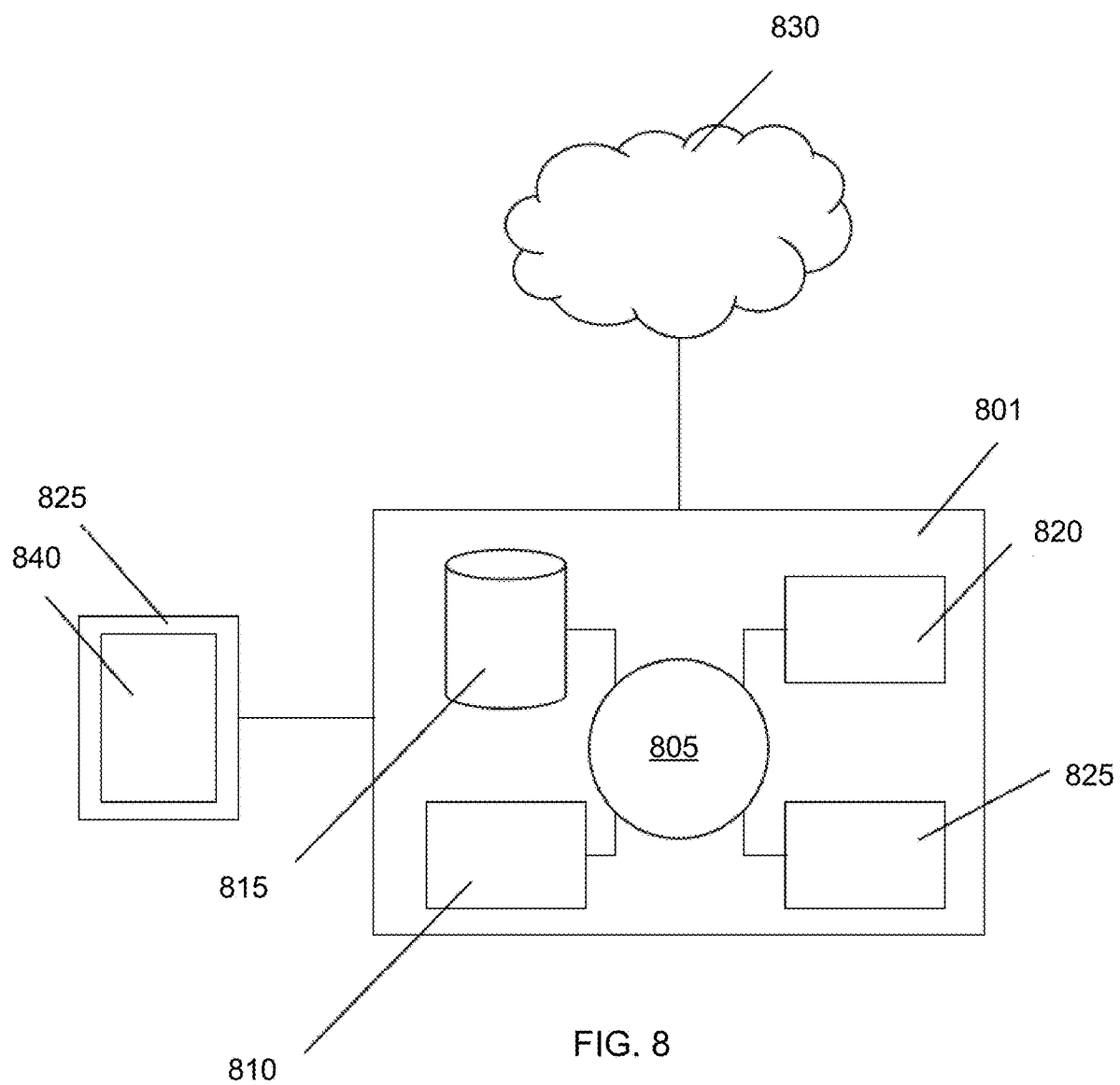
FIG. 8 depicts a computer system for implementing the methods of a health monitoring system in accordance with some embodiments of the present disclosure.

The present disclosure provides computer systems that are programmed to implement methods of the disclosure. FIG. 8 shows a computer system 801 that is programmed or otherwise configured to carry out executable instructions. The computer system may be programmed to process input data including sensor data to generate one or more trained model(s). The computer system may be programmed with one or more predictive model(s) or classifier(s) for analyzing input data (e.g., sensor data) to generate a prediction of a health status or health status change (e.g., deterioration of a patient's health status). The computer system 801 can regulate various aspects of the methods of the present disclosure, such as, for example, training the algorithm with the sensor data and corresponding health status label of a set of samples to generate a trained algorithm or classifier. The computer system 801 may determine the positive predictive value of a model or ensemble of models by analyzing a set of independent samples with the model(s) and comparing the actual results (e.g., feedback from stakeholders after the incident) of a health status change to the predicted health status change. The computer system 801 can be an electronic device of a user or a computer system that is remotely located with respect to the electronic device. The electronic device can be a mobile electronic device.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., a laptop or a smart phone). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processer adapted to execute the code, or the code can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases or other components shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, reports or results of health status monitoring or changes to health status. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, analyze sensor data to generate one or more predictions or predictive values with regards to health status or changes to health status.

It will be understood by those skilled in the art that the foregoing general description and the following detailed description are exemplary and explanatory of the disclosure and are not intended to be restrictive thereof.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

II. EXAMPLES

The following examples are included for illustrative purposes only and are not intended to limit the scope of the invention.

Example 1: Predetermined Dimensional Matrix

A 2D matrix is generated that comprises a matrix of filtered measured health parameters, derived parameters, and calculated clinical scores. This matrix is generated in real-time as new data enters the system's pre-processing and processing modules and is sent to the prediction module. This 2D matrix is referred to as a "predetermined matrix" because it has a fixed predetermined size, or time window, and has a predetermined frequency for data to be entered. In this case, the predetermined time window is a 2 hour window storing data at 3.33 millihertz (i.e. 1 data point per 5 minutes).

Multiple data streams are provided by three data acquisition devices. The input devices include a pulse oximeter, a blood pressure cuff, and an electrocardiogram. Each of these data streams is provided at different frequencies and have different processing requirements to be entered into the 2D matrix. In addition, raw data is filtered to remove data artifacts.

The vital signals are sampled. When the frequency of the vital signal being sampled is higher than the frequency selected for the 2D matrix, the data is down-sampled to fit the 2D matrix frequency. In this example, because the pulse oximeter obtains data at a frequency of 30 Hz, the data is down-sampled to the 3.33 millihertz frequency of the matrix. Some of the data is also up-sampled to fit the 2D matrix. In this example, the blood pressure cuff obtains data at a frequency of 0.2 millihertz, so the data is up-sampled to the 3.33 millihertz frequency of the matrix. The sampling is also utilized to fill gaps in the matrix created by data filtering that removes artifacts and other outliers.

The 2D matrix is filled with the final filtered data that has been sampled to the same frequency requirements of the matrix. The 2D matrix is also expanded with derived data. For example, an electrocardiogram is a picture of the electrical activity of the heart. Specific values from the electrocardiogram image are extracted be input into the matrix. For example, a standard 3 lead electrocardiogram gives a heart rhythm picture that can create the following derived vital signs: PQ interval, QRS complex width, QT interval, arrythmia state, and HR variability.

The 2D matrix is then expanded with the calculated risk score data. Multiple filtered vital signs are utilized to then create new data to be added to the 2D matrix. For example, by using the modified early warning score system, with the information available for each row of the 2D matrix, a score can be calculated. For example, a patient with pulse rate of 76, a respiratory rate of 24, and blood pressure of 135/76, may be assigned an early warning score of 1.

Once the matrix is prepared, additional tests are performed by an appending module prior to the matrix being sent to the predictive model. These tests ensure that the matrix can yield a high-quality prediction. In this example, the test to be sent for consumption is required to have at least 3 vital signs that have 80% of the matrix duration. If this threshold is passed, then the model is determined to have enough information to make a prediction.

The 2D matrix is also appended with static information about the sample including demographics, disease state, and other non-dynamic data (e.g., not sensor data). Then the matrix is provided to the predictive model 750 for consumption in order to generate a predicted health status (e.g., predicted mortality, medical emergency, health deterioration, or other change in health status).

Example 2: Ensemble Modelling Application

The matrix generated in Example 1 is provided to an ensemble modelling technique for analysis in order to generate a prediction of patient health status or change in health status. The matrix sent to the ensemble model contains both the health parameters and the static information.

In some embodiments, the ensemble method receives a predetermined matrix of data which includes health data captured at a predetermined frequency for a predetermined length of time. This matrix represents a holistic picture of the patient's condition which is analyzed by the model to make a proactive alert of changes to health status to the clinical teams.

The ensemble comprises two machine learning models: a CNN and a tree-based model. The ensemble architecture arranges the models parallel to each other, as they operate independently from each other in the real-time processing of the data. The models are developed to have similar computation time for the input matrix and compute faster than the frequency of the new input matrixes. The CNN model is configured to be more aggressive to predict changes in patient status, and the Tree-based model is configured to be more conservative and have lower false-positives in predicting changes. Static information is consumed differently based on the model type. For CNN, the static information is part of the matrix and no explicit call out is required, as the model will automatically integrate this data into its overall training and prediction. For a Tree, the static information is called out as categorical information and the tree architects its pathways to account for these different categories. The CNN is able to identify latent patterns of the static information on the prediction, versus the tree-based model is more logical in its pattern creation.

Both models make a prediction for each input predetermined dimensional matrix. The CNN model generates a CNN prediction label and the Tree-based model generates a tree prediction label. The prediction label is a 0, a 1, or a 2, based on if the model predicts that the patient will be stable, low risk, high risk, respectively. The predictions for both models are combined in a decision logic model to generate a final alert prediction while optimizing proactivity and false positive reduction using feature decomposition information. The final prediction is output to an alert generation module to generate one or more alerts based on the prediction data, as described herein. This combination strategy is configured based on each model's performance metrics (proactivity, false positive levels) to maximize proactivity below a maximum false positive level.

In one scenario, the CNN outputs a score of 1, but the Tree outputs a score of 0. Because the CNN is more aggressive, and the tree has not verified this prediction, the alert generation waits for the next prediction. In the following prediction, if the CNN still outputs a 1 or if the tree outputs a 1, then an alert is output. By adding this tree based check, the CNN prediction is verified or contradicted. In the scenario, that both the CNN and Tree output a 1, then the alert generation skips any delays or hysteresis and immediately send an alert, increasing proactivity.

In addition, this logic is adapted for higher risk alerts to integrate the predictions. When the CNN predicts a 2 and Tree predicts a 0, then the alert generation will wait for the Tree to predict at least a 1 before it outputs the alert. As a high criticality alert must have low false-positives, the speed of the CNN is utilized while not having to wait for the tree to have as high confidence before firing an alert. In the scenario that the Tree outputs a 2, but not the CNN, then an alert is output since the tree has a lower false positive than the CNN. However, this situation is unlikely as the CNN may be more aggressive in nature.

Example 3: Online Training

The ensemble model is fine-tuned for a hospital emergency room using an online training strategy. When alerts are sent out to the clinical teams, the teams then provide optional feedback on whether the alerts were helpful. This feedback is added to the pre-determined matrix as additional column. A matrix with the feedback is then stored as a new training dataset.

An online training session is triggered once 100 feedback responses have been received. The predictive models used by the ensemble modelling technique are re-trained using the new training dataset that includes the clinical team feedback. This retraining impacts the machine learning models that are a part of the ensemble. In this case, the CNN and tree-based method parameters are adjusted to account for the feedback received from clinicians. This allows the model to continue improving proactivity and/or accuracy through learning and adapting to new patient conditions based on feedback.

Example 4: Vital Sign Monitoring and Health Status Change Prediction

In some embodiments, a patient may come into a hospital with a cardiac disorder and need to be continuously monitored by clinical team. The current standard of monitoring may be using a machine which reads each vital sign, individually, and provides alerts if each vital sign is above or below a threshold. However, the hospital utilizes an improved system, as disclosed herein, for autonomously monitoring the patient through measuring and integrating all the data streams for multiple health parameters collected using one or more medical data acquisition devices. The system carries out pre-processing and processing of the data to deliver a high quality proactive alert that is pre-emptive of any health status change with higher accuracy and low false positives. This system does not need to wait until a vital signal crosses a specific user defined threshold, but rather processes the data holistically and proactively.

Because the patient needs continuous monitoring, they are placed on continuous respiratory rate monitoring, continuous ECG (cardiac electrical activity) monitoring, and require intermittent blood pressure readings every 30 min. The system takes into account that patient is a 65-year-old male, who has been diagnosed with congestive heart failure a few years ago.

These 3 data streams are monitored from a data acquisition device which flows to the cloud for real-time processing. All of these data streams come at various data rates (e.g., respiratory rate every 5 minutes, ECG analysis every minute, blood pressure measurement every 30 min). This information is down-sampled or up-sampled and placed into a 20 minute matrix to ensure the matrix is sufficiently full (80% of data). This matrix is a moving window matrix, meaning that as new data comes in, it adds the data in a FIFO (first in first out) basis.

The matrix is expanded to include other sub-analysis of the input data including blood pressure signal strength, motion artifacts, ECG PQRST wave values, heart rate variability, and respiratory rate tidal swing. For example, the matrix can include one or more columns corresponding to heart rate variability metrics. As another illustrative example, blood pressure can be broken down into additional metrics such as median blood pressure and signal strength, and ECG readings can be broken down into heart rate variability metrics, PQRST wave values, and other relevant metrics. In some embodiments, these additional breakdown metrics are added as additional columns in the matrix.

This matrix is then tagged or labelled with categorization information about the patient obtained from the patient's medical history and information. For example, CHF, 65-year-old, male, Dr. John Smith, in the Cardiac Department.

The 2D matrix capturing the patient's holistic status is then sent to the trained ensemble model. The trained model processes this matrix and is uses the 2-hour snapshot to make a prediction of a health status change for the patient. Since the model is an ensemble, it determines if the quality of the prediction is high enough to send the prediction. The model then leverages a class activation map algorithm to derive the key features and input data features that drove the successful prediction. This trained model, which has online-training capabilities, uses the information that this patient is in the Cardiac Department of this hospital, to use the specific prediction module fine-tuned for this area of implementation. Similar implementations may also be utilized in other departments, such as pulmonary, nephrology, OB-Gyn, oncology, pre-op, operation, post-op, medical ICU, surgical ICU, and cardiac ICU departments.

The patient's clinical condition may appear stable at a particular moment. Each the vitals individually may be within the ranges set by the clinician; thus, no alarms are firing. In a normal monitoring system, until a vital sign goes out of range, clinicians may not be alerted to the change in clinical condition. This may not provide enough time for a clinical response.

However, by utilizing the systems and method disclosed herein, the patient's current clinical condition leads to a prediction of upcoming change in health status despite individual vitals being within the normal reference range. In this example, predictions are clumped into 3 categories based on the predicted risk of the patient: 0=stable, 1=low clinical risk, 2=high clinical risk. In an example, a prediction has an output of 1 which is evaluated by an alert generation module which determines that this alert meets the requirements to send to first step of an escalation matrix (or a decision logic model). Since the prediction was a 1, it follows a specific escalation matrix to inform the first stage of caretakers with a recommendation of increasing observation. The prediction engine is processing and firing in real-time, so the alert generation engine is configured as a user experience layer to ensure the right amount of notifications get sent.

In this example, the notification states: "Patient is at risk for deterioration due to respiratory rate. Increased surveillance recommended" and is sent to the nursing head of the cardiac department. "Due to respiratory rate" is included based on the class activation map which determined that for this cardiac patient. The respiratory rate indicated the most risk of future health status change. As the prediction engine is real-time processing patient data, there are a constant stream of predictions going to the alert generation module. The module makes the determination to ensure that not all predictions are converted into an alert to ensure good user experience and high compliance to the alerts output by the system. This prediction may lead to multiple clinical actions. For example, a nurse may check on the patient and discusses with physician on duty. The nurse and physician agree that increased vigilance is beneficial and the physician increases the amount of monitoring by adding pulse oximetry and increasing BP frequency to every 15 minutes. The nurse responds to the notification saying it was "helpful" providing feedback to the online-training aspect of the system. This feedback is stored in the system for future scheduled retraining by the online-training system. Online-training is adjusted to be automatically conducted on a weekly basis, integrating new patient data and the feedback for the quality of the predictions on a batch wise basis and further the base ensemble model to align to clinical requirements.

The clinical changes to increase monitoring create new information and data streams which are absorbed into the same system. The system is designed to function with changing data streams and thus integrates the new data streams, appropriately sampling the data, removing noise, and creating new 2D matrices that can be consumed by the prediction system. The system now analyses the new holistic picture of the patient, again looking to make a prediction of a health status change. Due to the successfully predicted respiratory distress, the patient begins to mildly over-compensate. At this time the patients respiratory rate goes outside the alarm limit, but the nurse checks and verifies that it is still borderline since the oxygen levels are being maintained and thus determines the patient as compensating successfully, without needing intervention.

Later, despite being within range, the patient's blood oxygen begins to fluctuate as patient is unable to easily maintain blood oxygenation. The levels are still within the range set by standard physiology, thus not firing any threshold alarms. The patient continues to work hard to stay within the physiological limits, but standard alarming system cannot see this. The predictive system, through the analysis of the properly collected, sampled, and refined matrix, and processed by the predictive algorithm is able to see these minute patterns in physiology.

Later, after another 15 minutes, the system determines that the risk of patient status change is even higher, and the prediction module predicts a risk score of 2. The hysteresis for a sending a notification for a risk score of 2 is higher due to the larger escalation, thus the alert system waits for another prediction to verify the risk. After the alter system receives another prediction of risk score 2, it fires a new notification. This time due to higher criticality, the notification takes the higher escalation pathway. The on-duty physician is informed directly along with the nurse. The notification states: "Patient is suspect for significant change in status in 20 minutes due to respiratory rate and blood oxygen levels". Again the "due to respiratory rate and blood oxygen levels' is determined by the class activation map in the system. This notification allows the nursing and clinical team to intervene of the patient who was decompensating but still within the clinical ranges of the alarms set. They immediately follow proactive medications (e.g., place patient on high flow oxygen, etc). This increases oxygenation, reduces respiratory rate to original levels, and prevent the patient decompensation pathway which often leads to impending cardiac arrest.

Example 5: Ensemble Modelling Performance Compared to Benchmark Models

The ensemble modelling approach was compared against single-model approaches to determine if performance was improved. The ensemble approach was implemented towards the conversion of real-time patient data to predict clinical labels with better timeliness and lower false positives compared to traditional modeling techniques.

To measure this performance, 5 different models were developed for comparison including benchmark techniques and individual neural network models. Each of these models was trained on 75,115 pre-determined dimensional matrixes created from real-world patients being monitored. A testing dataset was created with an independent 4,223 matrixes. The matrixes contained 2-hour windows of data sampled at an interval of every 5 minutes.

The matrixes were processed to ensure the matrixes were ready to be trained. Data was up-sampled or down-sampled to ensure completeness of the matrix. The matrix went through normalization and were checked to have at least 80% of data availability from at least 3 or more sensors.

The matrixes had each row labeled with a holistic clinical status score based on the vital signs, and for this training, the modified early warning score was utilized as the clinical label. Two consecutive modified early warning scores of greater than 3 was defined as the clinical gold standard that served as the basis for a true positive. This definition was determined by the clinical EWS implementation standard for escalating a notification to clinicians for action. Based on this true-positive definition, the entire dataset had 15% of the matrixes meet the true-positive definition.

Each model was trained against the test subjects with the goal of making a prediction of a true positive twenty minutes ahead of the actual escalation of patient condition.

All the models were then tested on the test dataset. The models were compared against each other to compare performance with this fixed prediction time. Performance was investigated through key metrics such as precision, recall, and F1 score. These metrics were chosen for their ability to represent performance in lines of the needs of healthcare professionals and allows for the metrics to not be impacted by imbalance in the dataset.

The models were evaluated for performance metrics of precision, recall, and F1 score. Precision represented the model's ability to maintain low false positives (higher number=lower false positives). Recall represented the model's ability to be timely and catch all the true-positives without waiting for more data to enter the system and increase confidence. (higher number=better timeliness). F1 score was provided as a combined normalization score of both precision and recall and serves as a metric to compare performance (higher number=overall better performance).

The results are shown in Table 1.

| Model | Precision | Recall | F1 Score |
| --- | --- | --- | --- |
| Logistic regression | 0.75 | 0.75 | 0.75 |
| 2D-CNN | 0.84 | 0.84 | 0.83 |
| 1D-CNN | 0.88 | 0.91 | 0.89 |
| XGBoost Tree | 0.90 | 0.88 | 0.89 |
| Ensemble | 0.92 | 0.91 | 0.92 |

Table 1 shows individual models for logistic regression, 2D-CNN, 1D-CNN, and a tree model (XGBoost Tree) as compared to an ensemble approach based on precision, recall, and F1 score performance metrics. The data in Table 1 highlights the significant improvement in the predictive capability of the data processing and ensemble modeling technique over benchmarks or traditional neural network models. It is important to note the context of making incremental improvements of scores that already are in the high 80's and 90's. Every 1% improvement in high volume datasets represents a massive number of patients impacted by the improved performance and is very challenging to achieve.

The other models are provided as benchmarks to showcase the complexity of achieving a medical-grade prediction algorithm using standard linear regression or standard 2D-CNN technique.

The results shows that XGBoost and tree methodology achieve higher precision than the more aggressive 1D-CNN which has higher false positives. However, the strength of the 1D-CNN is its significantly higher recall, which means it captures a significantly higher number of the predictions with the same prediction window. This showcases its timeliness as it has good performance in catching the true-positives even 20 minutes ahead of the true-positive event without waiting for additional data. As shown in Table 1, the F1 score for both models is the same at 0.89 because precision and recall are always a tradeoff, as increasing one causes the other to fall.

The data shows the ensemble method is able to outperform both the CNN and the Tree Model and, unexpectedly, perform better in accuracy than either one model individually. The ensemble technique achieves higher precision than either 1 model together: 0.92 versus 0.90 for XGboost or 0.88 for 1D-CNN, which means the ensemble achieves even a lower false positive than both models individually, and by a large margin (over 4% more than the normal CNN modeling technique).

Even more importantly, the ensemble technique is able to achieve this while maintaining the recall of the 1D-CNN of 0.91 and not lowering to the recall of the XGboost methodology.

The strong performance in both of these metrics brings an overall combined F1 score of 0.92 which is more confident than the 0.89 of either individual model. This improved performance is especially significant because both individual models are already quite high in precision, recall, and F1 score, where adjustments to the modeling technique can even lower performance. This improved performance is particularly impactful in the healthcare space where each percentage point change in clinical confidence in the patient status changes can mean the difference in whether a patient's life can be saved.

These initial findings can be further improved with additional training data, with the expansion of the pre-determined matrix with calculated data, with additional clinical labels, with the integration of static information to better segment the dataset, and online-training techniques to modify the base algorithm for the patient population.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A computer-implemented status monitoring and future event prediction system comprising a data analytics subsystem comprising a computing device comprising a processor, a memory, and an operating system configured to perform executable instructions, wherein the computing device is operative to:
   receive, by the computing device, an electronic signal comprising health data representative of a plurality of health parameters of one or more patients from one or more medical data acquisition devices;
   filter, by the computing device, the electronic signal comprising the health data to eliminate one or more outliers;
   create, using the computing device, a predetermined dimensional matrix representative of a plurality of samples obtained from a moving window of the filtered health data representative of the plurality of health parameters of the one or more patients in a predefined interval;
   process, using the computing device, one or more samples selected from the plurality of samples of the predetermined dimensional matrix based on a predefined condition;
   label, by the computing device, the predetermined dimensional matrix upon processing of the one or more samples using one or more clinical scoring techniques; and
   analyze, by the computing device, the labelled predetermined dimensional matrix using an ensemble modelling technique to generate a prediction of a future event comprising a predicted health status of the one or more patients in real-time, wherein the future event is predicted to occur at least a minimum period of time after a time period corresponding to the moving window of filtered health data;
   wherein the ensemble modelling technique comprises a first model configured for higher recall than precision and a second model configured for higher precision than recall, wherein the ensemble modelling technique has a higher precision than the first model and a higher recall than the second model, wherein the ensemble modelling technique analyzes the labelled predetermined dimensional matrix using the first model configured for higher recall than precision and the second model configured for higher precision than recall to generate individual predictions and applies a rule-based decision logic to integrate the individual predictions generated by the first model and the second model into the predicted health status of the one or more patients in real-time.

2. The system of claim 1, wherein the first model comprises a neural network.

3. The system of claim 1, wherein the second model comprises a tree model.

4. The system of claim 1, wherein the minimum period of time is at least 5 minutes after the time period corresponding to the moving window of filtered health data.

5. The system of claim 1, wherein the data analytics subsystem is hosted on a cloud server, a local server, the one or more medical data acquisition devices, or a combination thereof.

6. The system of claim 1, wherein the plurality of health parameters comprises heart rate, blood oxygen, electrocardiogram, respiratory rate, blood pressure, temperature, or a combination thereof.

7. The system of claim 1, wherein the one or more outliers comprises at least one of additional movements of the one or more patients, misplacement of one or more sensors, one or more data artefacts, one or more noises, or a combination thereof.

8. The system of claim 1, wherein the one or more medical data acquisition devices comprises a bedside monitoring device comprising at least one communication medium to receive the plurality of health parameters from one or more sensors and a display interface.

9. The system of claim 8, wherein the one or more medical data acquisition devices are configured to:
    collect the health data representative of the plurality of health parameters from the one or more patients through the one or more sensors; and
    display the health data collected from the one or more patients on a display interface via a predefined icon from a plurality of designated icons.

10. The system of claim 1, wherein the predefined condition comprises selection of at least one sample for which the plurality of health parameters passes a predefined threshold value for a predefined time period.

11. The system of claim 1, wherein the computing device is further operative to process static information associated with the one or more patients, wherein the static information comprises patient demographics, patient health condition or one or more clinical notes.

12. The system of claim 1, wherein the ensemble modelling technique comprises a dilated causal convolution network, a tree-based gradient boosted technique, a recurrent neural network, a graph neural network, a support vector machine classifier, a logistic regression technique, a k-nearest neighbor classifier, or any combination thereof.

13. The system of claim 1, wherein the computing device is further operative to implement an online training technique to fine-tune a prediction model corresponding to one or more clinical and operational requirements of an area of implementation or a patient health condition.

14. The system of claim 1, wherein the computing device is further operative to generate one or more predictive alerts for the one or more patients based on the prediction of the future event comprising the predicted health status of the one or more patients.

15. The system of claim 14, wherein the one or more predictive alerts generated are described with one or more contributing input features using a class activation map technique, wherein the class activation map technique determines the one or more input contributing features responsible for successful prediction of clinical scores in multiclass prediction.

16. The system of claim 14, wherein the computing device is further operative to add hysteresis for providing one or more escalation processes based on a plurality of prediction classes.

17. The system of claim 14, wherein the computing device is further operative to:
    transmit the one or more predictive alerts to one or more corresponding stakeholders for creating awareness associated with the health status of the one or more patients based on the predictive value; and
    prioritize a list of the one or more patients with a predictive value higher than a predetermined predictive value based on transmission of the one or more predictive alerts.

18. The system of claim 14, wherein the computing device is further operative to transmit a signal comprising the predicted health status of the one or more patients and the one or more predictive alerts to one or more handheld computing devices and one or more handheld electronic devices associated with at least one of the one or more patients or one or more stakeholders associated with the one or more patients, wherein the one or more stakeholders comprises at least one of a caregiver, a nurse, a healthcare practitioner, or any combination thereof.

* * * * *